United States Patent
Park et al.

(10) Patent No.: US 9,985,222 B2
(45) Date of Patent: May 29, 2018

(54) ORGANIC COMPOUND, AND ORGANIC THIN FILM AND ELECTRONIC DEVICE

(71) Applicant: Samsung Electronics Co., Ltd., Suwon-si, Gyeonggi-do (KR)

(72) Inventors: Jeong Il Park, Seongnam-si (KR); Eun Kyung Lee, Seoul (KR)

(73) Assignee: Samsung Electronics Co., Ltd., Gyeonggi-do (KR)

(*) Notice: Subject to any disclaimer, the term of this patent is extended or adjusted under 35 U.S.C. 154(b) by 0 days. days.

(21) Appl. No.: 14/738,092

(22) Filed: Jun. 12, 2015

(65) Prior Publication Data

US 2015/0372241 A1     Dec. 24, 2015

(30) Foreign Application Priority Data

Jun. 23, 2014 (KR) .................. 10-2014-0076625
May 15, 2015 (KR) .................. 10-2015-0068129

(51) Int. Cl.
| H01L 51/00 | (2006.01) |
| H01L 51/05 | (2006.01) |
| C07D 495/14 | (2006.01) |
| C07D 495/04 | (2006.01) |
| C07D 333/50 | (2006.01) |

(52) U.S. Cl.
CPC ........ *H01L 51/0074* (2013.01); *C07D 333/50* (2013.01); *C07D 495/04* (2013.01); *C07D 495/14* (2013.01); *H01L 51/0558* (2013.01)

(58) Field of Classification Search
CPC ............. H01L 51/0074; H01L 51/0512; H01L 51/105; H01L 51/0516; C07D 495/04; C07D 495/14; C07D 333/50
See application file for complete search history.

(56) References Cited

U.S. PATENT DOCUMENTS

| 7,816,673 | B2 | 10/2010 | Park et al. | |
| 8,658,805 | B2 | 2/2014 | Park et al. | |
| 2006/0214155 | A1* | 9/2006 | Ong | C07D 487/04 257/40 |
| 2009/0043113 | A1 | 2/2009 | Park et al. | |
| 2013/0035464 | A1* | 2/2013 | Facchetti | C08G 61/123 526/240 |
| 2013/0109821 | A1* | 5/2013 | He | C07D 495/22 526/256 |
| 2013/0230316 | A1 | 9/2013 | Hussain et al. | |
| 2013/0320316 | A1 | 9/2013 | Hussain et al. | |
| 2013/0277657 | A1 | 10/2013 | Park et al. | |

FOREIGN PATENT DOCUMENTS

| JP | 11144866 A | * | 5/1999 | |
| JP | 2006290192 A | | 10/2006 | |
| JP | 2007197400 A | | 8/2007 | |
| JP | 2007317984 A | | 12/2007 | |
| JP | 2009141338 A | | 6/2009 | |
| JP | 2009182034 A | * | 8/2009 | |
| JP | 2010045281 A | * | 2/2010 | |
| JP | 2010087408 A | | 4/2010 | |
| JP | 2010177641 A | | 8/2010 | |
| JP | 2010177642 A | | 8/2010 | |
| JP | 2010205815 A | * | 9/2010 | |
| JP | 2010205982 A | | 9/2010 | |
| JP | 2011165747 A | * | 8/2011 | |
| JP | 2013253080 A | | 12/2013 | |
| KR | 20080054553 A | | 6/2008 | |
| KR | 20120052062 A | * | 5/2012 | |
| KR | 20130050266 A | | 5/2013 | |
| WO | WO-9521170 | | 8/1995 | |
| WO | WO-20090009790 A1 | | 1/2009 | |
| WO | WO 2011131936 A1 | * | 10/2011 | ........... C07D 333/18 |
| WO | WO 2013002217 A1 | * | 1/2013 | ........... C07D 409/14 |
| WO | WO 2014092362 A1 | * | 6/2014 | ........... C07D 495/04 |

OTHER PUBLICATIONS

Yoshii, R., "Synthetic Strategy for Low-Band Gap Oligomers and Homopolymers Using Characteristics of Thiophene-Fused Boron Dipyrromethene." Macromolecules 47.11 (2014): 3755-3760.*
Lukoyanova, O., "Donor-Acceptor Intermediates and Low-Bandgap Polymers by Electropolymerization of Thienoazaborines." Macromolecules 44.12 (2011): 4729-4734.*
Miyasaka, M., "Noncovalent interactions in the asymmetric synthesis of rigid, conjugated helical structures." Angewandte Chemie International Edition 48.32 (2009): 5954-5957 plus Supplemental Information p. S1-S49.*
Saito, K., "Palladium-Catalyzed Construction of Heteroatom-Containing π- Conjugated Systems by Intramolecular Oxidative C_ H/C_ H Coupling Reaction." Chemistry—A European Journal 21.23 (2015): 8365-8368.*
ProQuest Dialog JP 201165747 A English Machine Translation p. 1-39; Jul. 15, 2016.*
ProQuest Dialog JP 11144866 A English Machine Translation p. 1-26; Jul. 20, 2016.*
ProQuest Dialog JP 2009182034 A English Machine Translation p. 1-27; Jul. 20, 2016.*
ProQuest Dialog JP 2010045281 A English Machine Translation p. 1-48; Jul. 20, 2016.*
ProQuest Dialog JP 2010205815 A English Machine Translation p. 1-52; Jul. 20, 2016.*
K-PION KR 2012052062 English Machine Translation p. 1-49; Jul. 20, 2016.*
ProQuest Dialog WO 2013002217 A1 English Machine Translation p. 1-79; Jul. 20, 2016.*
ProQuest Dialog WO 2014092362 A1 English Machine Translation p. 1-37; Jul. 20, 2016.*
Nakano, M., "Naphtho [2, 3-b: 6, 7-b'] dichalcogenophenes: syntheses, characterizations, and chalcogene atom effects on organic field-effect transistor and organic photovoltaic devices." Chemistry of Materials 24.1 (2011): 190-198.*

(Continued)

*Primary Examiner* — John M Mauro
(74) *Attorney, Agent, or Firm* — Harness, Dickey & Pierce, P.L.C.

(57) ABSTRACT

An organic compound is represented by Chemical Formula 1, and an organic thin film, an organic thin film transistor, and an electronic device include the organic compound.

5 Claims, 1 Drawing Sheet

(56) References Cited

OTHER PUBLICATIONS

Mitsui, C.,"Dinaphtho [1, 2-b: 2', 1'-d] chalcogenophenes: Comprehensive Investigation of the Effect of the Chalcogen Atoms in the Phenacene-Type π-Electronic Cores." Chemistry of Materials 25.20 (2013): 3952-3956.*

JP 2009182034 A English machine translation Proquest Dialog Jul. 28, 2017 p. 1-27.*

Niebel, C., "Thienoacene dimers based on the thieno [3, 2-b] thiophene moiety: synthesis, characterization and electronic properties." Journal of Materials Chemistry C 3.3 (2015): 674-685.*

V. V. Ghaisas et al., "Thiophene Isosters of of Carcinogenic Hydrocarbons: Part III—4:I0—Dimethylthionaphtheno—(6:5-b)—thionaphthene & 6:I2-Dimethyl-benzo (I:2-b, 4:5-b)-dithionaphthene", Korea Institute of Science and Technology Information, 1955, Journal of Scientific & Industrial Research, vol. 14B, pp. 11-13.

Ronald E. Banks et al., "Nitroxide Chemistry. Part V.[1] Reactions Between Bistrifluoromethyl Nitroxide and Alkylbenzenes; Mechanism of Formation of Carbonyl Compounds", J.C.S. Perkin I, Jan. 1973, pp. 1092-1099.

V. N. Gogte, "PMR Spectra of Some Heteroaromatic Compounds Containing Hindered Methyl Groups", Indian Journal of Chemistry, vol. 9, Feb. 1971, pp. 121-124.

* cited by examiner

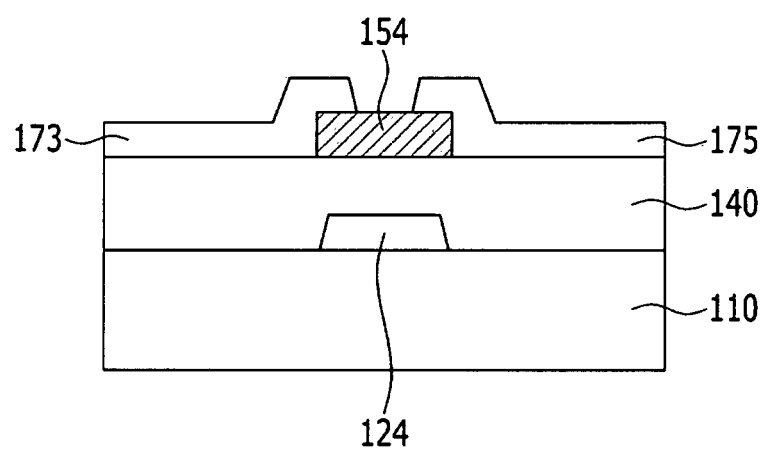

ORGANIC COMPOUND, AND ORGANIC THIN FILM AND ELECTRONIC DEVICE

CROSS REFERENCE TO RELATED APPLICATION

This application claims priority to and the benefit of Korean Patent Application No. 10-2014-0076625 filed in the Korean Intellectual Property Office on Jun. 23, 2014 and Korean Patent Application No. 10-2015-0068129 filed in the Korean Intellectual Property Office on May 15, 2015, the entire contents of which are incorporated herein by reference.

BACKGROUND

1. Field

Example embodiments provide an organic compound, an organic thin film, and an electronic device.

2. Description of the Related Art

A flat panel display (e.g., a liquid crystal display (LCD), an organic light emitting diode (OLED) display, or an electrophoretic display) includes multiple pairs of field generating electrodes and an electro-optical active layer interposed therebetween.

The liquid crystal display (LCD) includes an electro-optical active layer of a liquid crystal layer, and the organic light emitting diode (OLED) display includes an electro-optical active layer of an organic emission layer.

One of paired field generating electrodes are generally connected to a switch and applied with an electrical signal, and the electro-optical active layer transforms the electrical signal to an optical signal to display an image.

The flat panel display includes a three-terminal element of a thin film transistor (TFT) as a switch, and it also includes a gate line transferring a scan signal for controlling the thin film transistor and a data line transferring a data signal to be applied to a pixel electrode.

Among the thin film transistors, an organic thin film transistor (OTFT) including an organic semiconductor (e.g., a low molecular compound or a polymer) instead of the inorganic semiconductor (e.g., silicon (Si)) has been actively researched.

The organic thin film transistor may be shaped in a fiber or a film form according to the organic material characteristic, so it may has drawn attention as a core element for a flexible display device.

The organic thin film transistor may be manufactured using a solution process (e.g., inkjet printing), and may be more easily applied to a large area flat panel display where a deposition process has a limit.

SUMMARY

Example embodiments provide an organic compound that is applicable to an electronic device, for example, an organic thin film transistor.

Example embodiments also provide an organic thin film including the organic compound.

Example embodiments also provide an electronic device including the organic thin film.

According to example embodiments, an organic compound is represented by the Chemical Formula 1.

A-B  [Chemical Formula 1]

In Chemical Formula 1,
each of an A moiety and a B moiety are independently one of a condensed polycyclic group having four or more fused rings, and are represented by one of the Chemical Formulae 2 to 4,

[Chemical Formula 2]

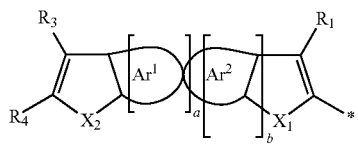

[Chemical Formula 3]

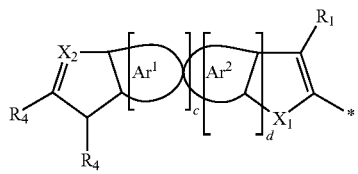

[Chemical Formula 4]

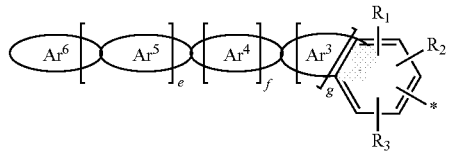

wherein, in Chemical Formulae 2 to 4,
each of $Ar^1$ to $Ar^6$ are independently one of a substituted or unsubstituted 5-membered ring and a substituted or unsubstituted 6-membered ring,
at least one of $Ar^3$ to $Ar^6$ is a substituted or unsubstituted 5-membered ring having a heteroatom,
each of $Ar^1$ and $Ar^2$ forms a fused ring with an adjacent ring,
each of $Ar^3$ to $Ar^6$ forms a fused ring with an adjacent ring,
each of $X^1$ and $X^2$ are independently one of O, S, Se, Te, and $NR^a$,
each of $R^1$ to $R^4$ and $R^5$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{33}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heteroaryl group, a substituted or unsubstituted $C_2$ to $C_{30}$ alkenyl group, a substituted or unsubstituted $C_2$ to $C_{30}$ alkynyl group, a hydroxy group, a halogen atom, and a combination thereof,
each of a to g are independently integers ranging from 0 to 3, provided that a+b≥2, c+d≥2, and e+f+g≥2, and
* indicates a linking point.

Each of the $Ar^1$ to $Ar^6$ may independently be one of a substituted or unsubstituted benzene ring and a substituted or unsubstituted heterocyclic group.

The at least one of the $Ar^1$ and $Ar^2$ may be a heterocyclic group including one of O, S, Se, Te, and $NR^a$, and at least one of the $Ar^3$ to $Ar^6$ may be a heterocyclic group including one of O, S, Se, Te, and NW, wherein $R^a$ is one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heteroaryl group, a substituted or unsubstituted $C_2$ to $C_{30}$ alkenyl group, a substituted or unsubstituted $C_2$ to $C_{30}$ alkynyl group, a hydroxy group, a halogen atom, and a combination thereof.

Each of the A moiety and the B moiety may be independently one of the groups listed in the Group 1.

[Group 1]

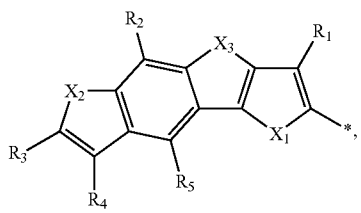

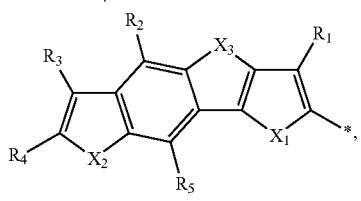

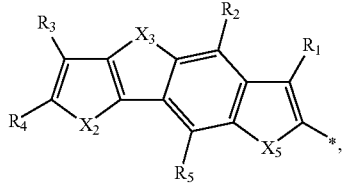

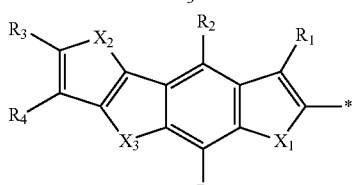

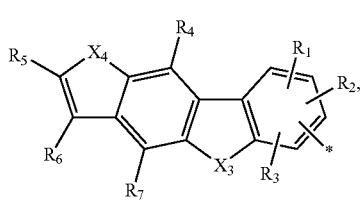

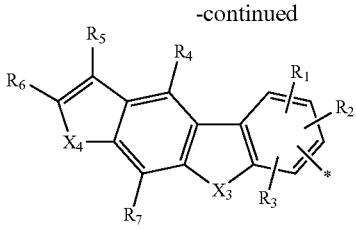

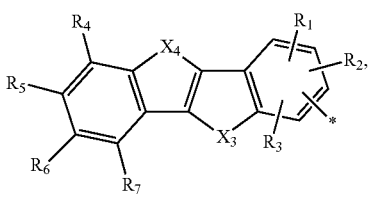

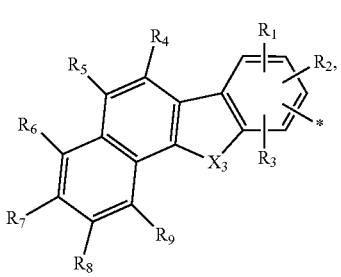

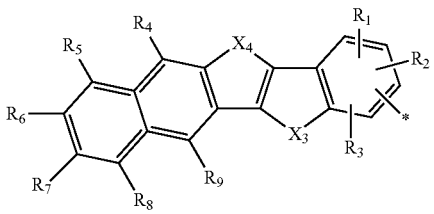

In Group 1, each of $X^1$ to $X^4$ are independently one of O, S, Se, Te, and $NR^a$, each of $R^1$ to $R^9$ and $R^a$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heteroaryl group, a substituted or unsubstituted $C_2$ to $C_{30}$ alkenyl group, a substituted or unsubstituted $C_2$ to $C_{30}$ alkynyl group, a hydroxy group, a halogen atom, and a combination thereof, each of $R^1$ to $R^9$ are independently present or two adjacent groups are fused to each other to provide a fused ring, and

* indicates a linking point.

The A moiety and the B moiety of Chemical Formula 1 may be twisted, and not on the same plane.

The organic compound may be one of compounds listed in the Group 2.

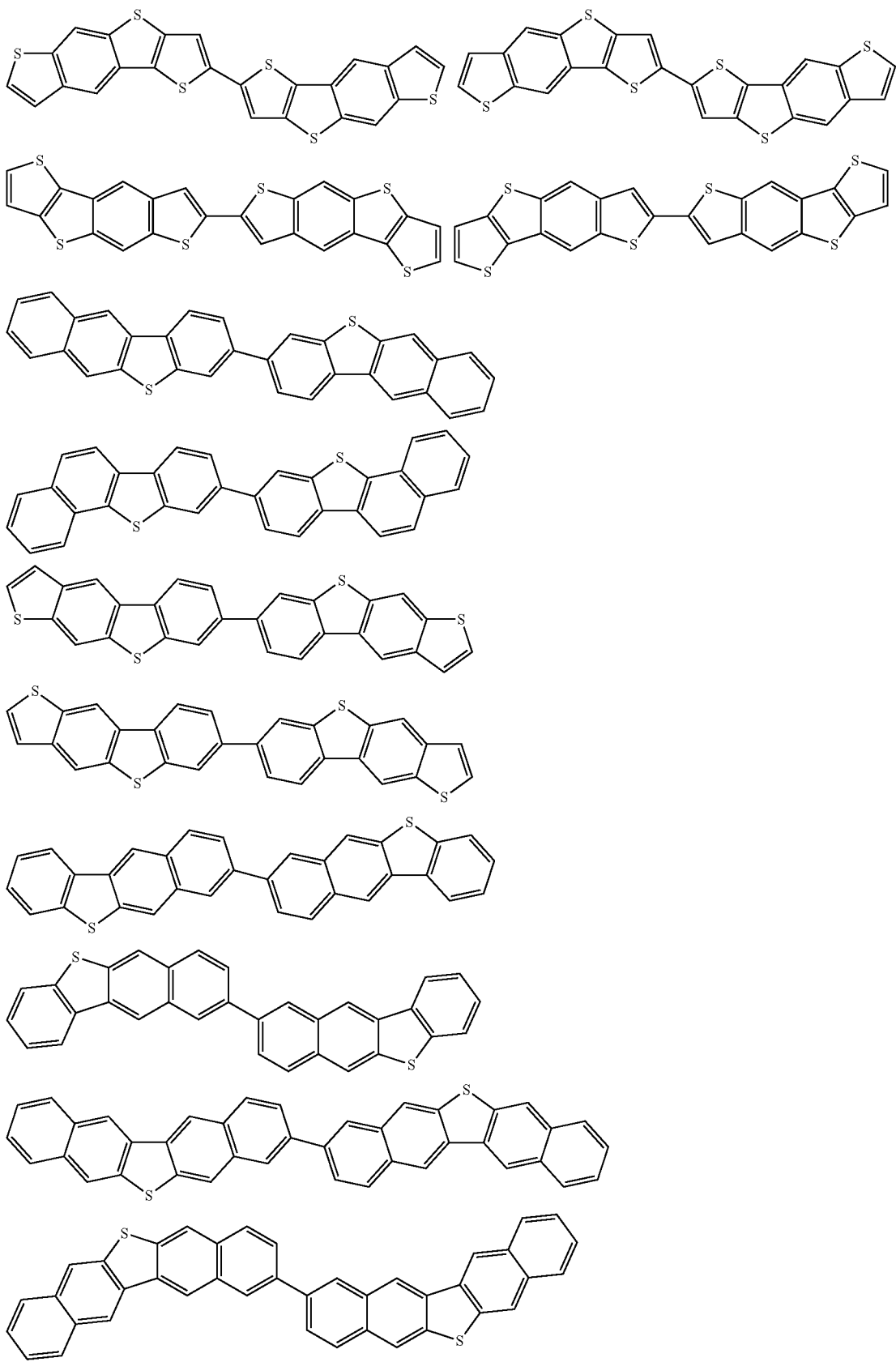
[Group 2]

-continued
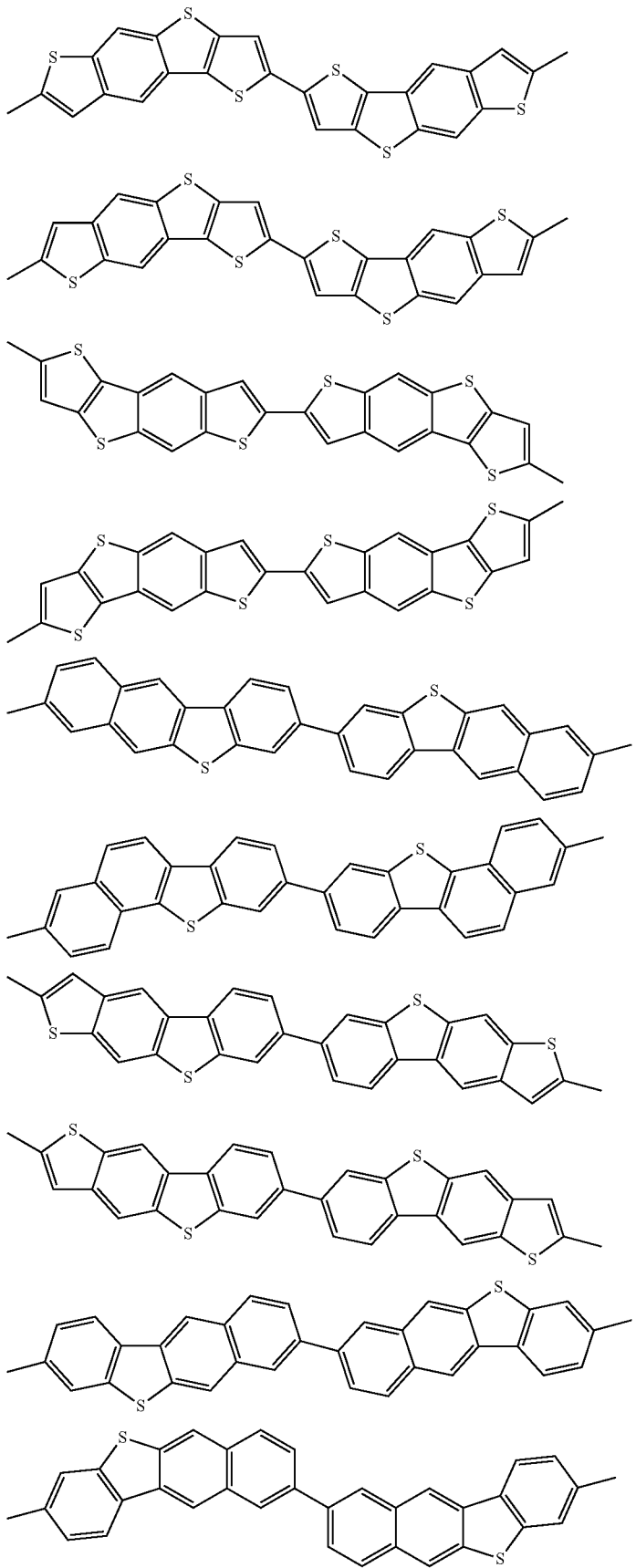

-continued
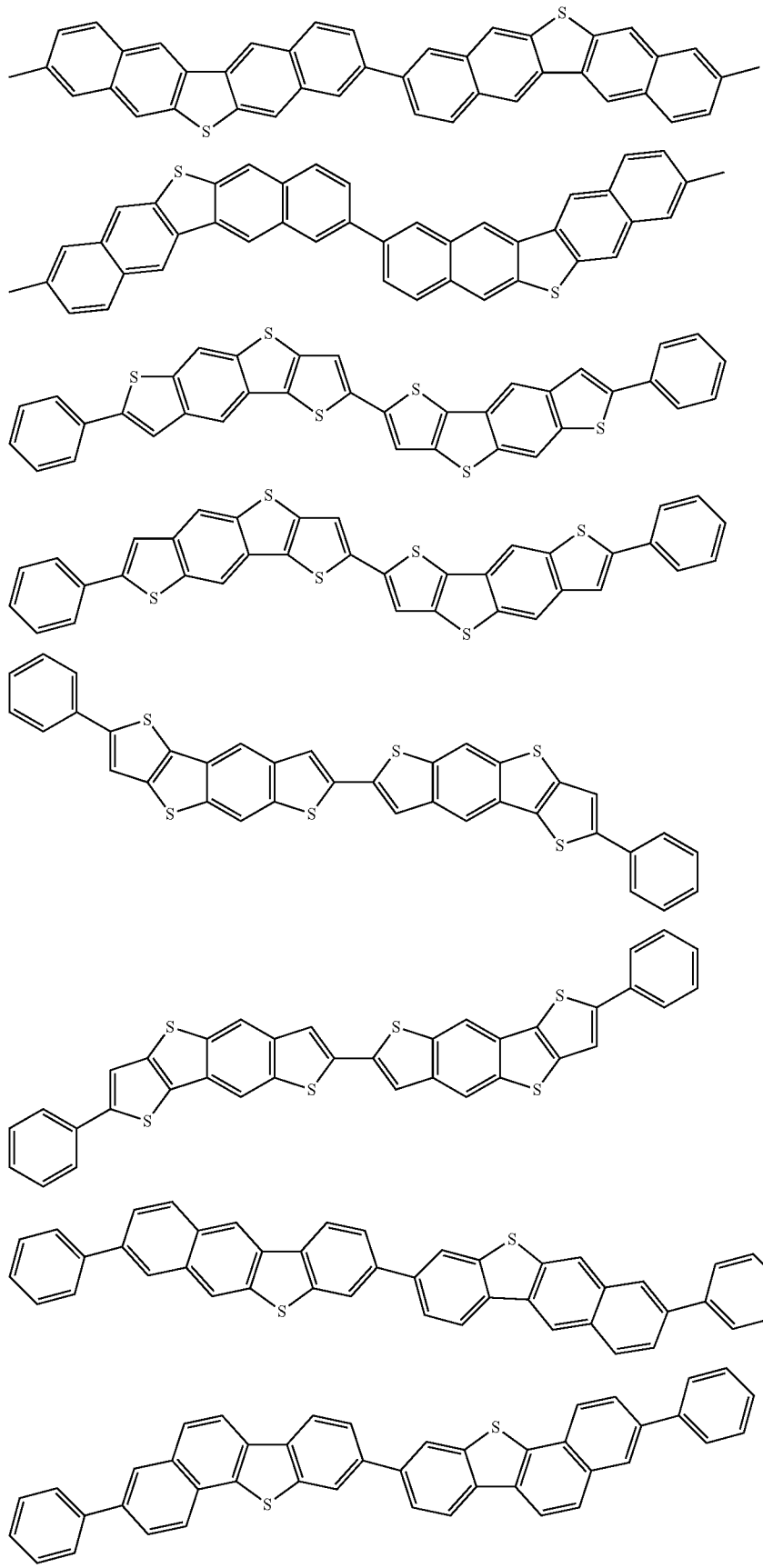

-continued

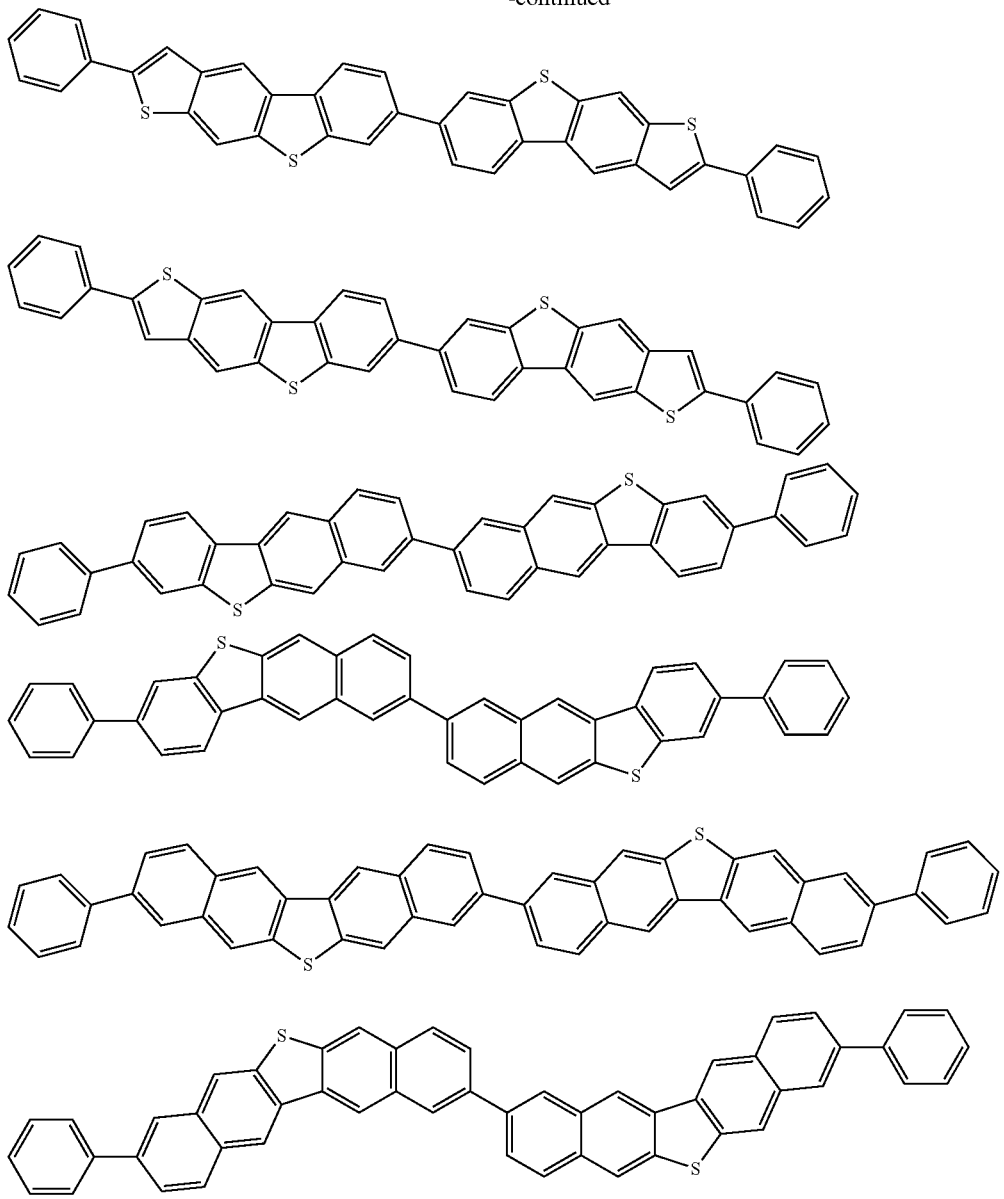

According to example embodiments, an organic thin film includes the organic compound.

According to example embodiments, an organic thin film transistor includes a gate electrode, an organic semiconductor overlapping the gate electrode, and a source electrode and a drain electrode electrically connected to the organic semiconductor, wherein the organic semiconductor includes an organic compound represented by the Chemical Formula 1.

A-B  [Chemical Formula 1]

In Chemical Formula 1, each of an A moiety and a B moiety are independently a condensed polycyclic group having four or more fused rings, and are represented by one of the Chemical Formulae 2 to 4,

[Chemical Formula 2]

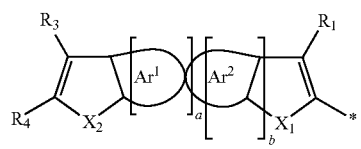

[Chemical Formula 3]

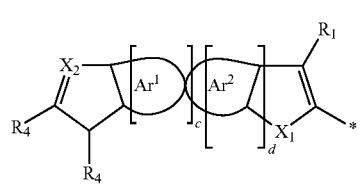

[Chemical Formula 4]

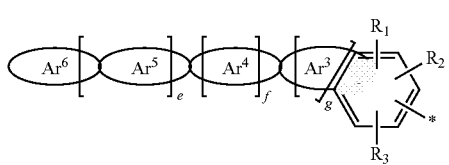

wherein, in Chemical Formulae 2 to 4, each of $Ar^1$ to $Ar^6$ are independently one of a substituted or unsubstituted 5-membered ring or a substituted or unsubstituted 6-membered ring, at least one of $Ar^3$ to $Ar^6$ is a substituted or unsubstituted 5-membered ring having a heteroatom, each of $Ar^1$ and $Ar^6$ forms a fused ring with an adjacent ring, each of $Ar^3$ to $Ar^6$ forms a fused ring with an adjacent ring, each of $X^1$ and $X^2$ are independently one of O, S, Se, Te, and $NR^a$, each of $R^2$ to $R^4$ and $R^a$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_2$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heteroaryl group, a substituted or unsubstituted $C_2$ to $C_{30}$ alkenyl group, a substituted or unsubstituted $C_2$ to $C_{30}$ alkynyl group, a hydroxy group, a halogen atom, and a combination thereof, each of a to g are independently integers ranging from 0 to 3, provided that a+b≥2, c+d≥2, and e+f+g≥2, and

* indicates a linking point.

Each of the $Ar^1$ to $Ar^6$ may be independently one of a substituted or unsubstituted benzene ring and a substituted or unsubstituted heterocyclic group. The at least one of the $Ar^1$ and $Ar^2$ may be a heterocyclic group including one of O, S, Se, Te, and $NR^a$, and at least one of the $Ar^3$ to $Ar^6$ may be a heterocyclic group including one of O, S, Se, Te, and $NR^a$, wherein $R^a$ is one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heteroaryl group, a substituted or unsubstituted $C_2$ to $C_{30}$ alkenyl group, a substituted or unsubstituted $C_2$ to $C_{30}$ alkynyl group, a hydroxy group, a halogen atom, and a combination thereof.

Each of the A moiety and the B moiety of Chemical Formula 1 may independently be one of groups listed in the Group 1.

[Group 1]

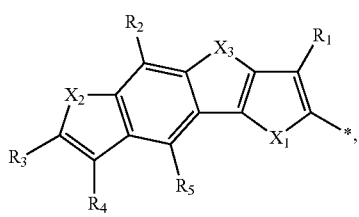

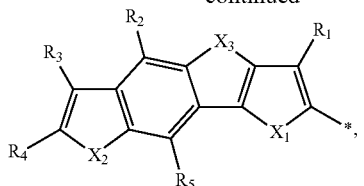

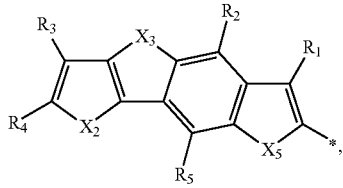

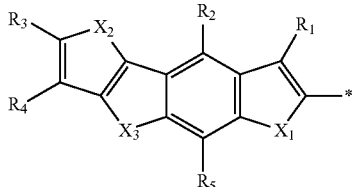

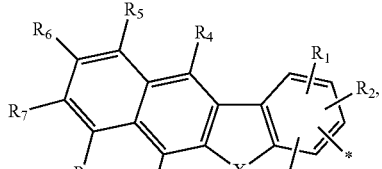

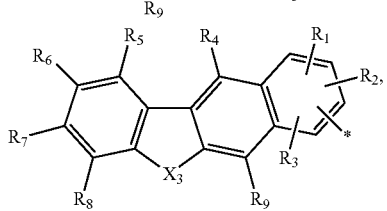

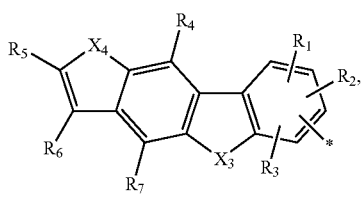

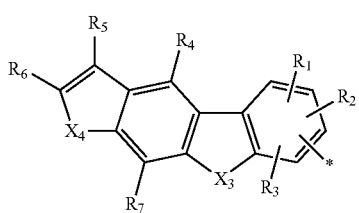

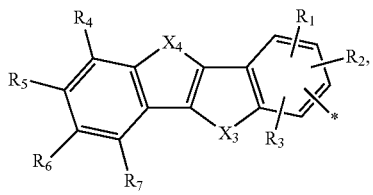

-continued

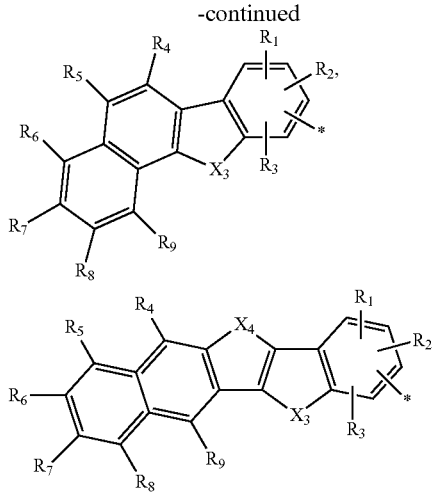

In Group 1, each of $X^1$ to $X^4$ are independently one of O, S, Se, Te, and $NR^a$, each of $R^1$ to $R^9$ and $R^a$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heteroaryl group, a substituted or unsubstituted $C_2$ to $C_{30}$ alkenyl group, a substituted or unsubstituted $C_2$ to $C_{30}$ alkynyl group, a hydroxy group, a halogen atom, and a combination thereof, each of $R^2$ to $R^9$ are independently present or two adjacent groups are fused to each other to provide a fused ring, and \* indicates a linking point.

The A moiety and the B moiety of Chemical Formula 1 may be twisted and not on the same plane.

The organic compound may be one of the compounds listed in the Group 2.

[Group 2]

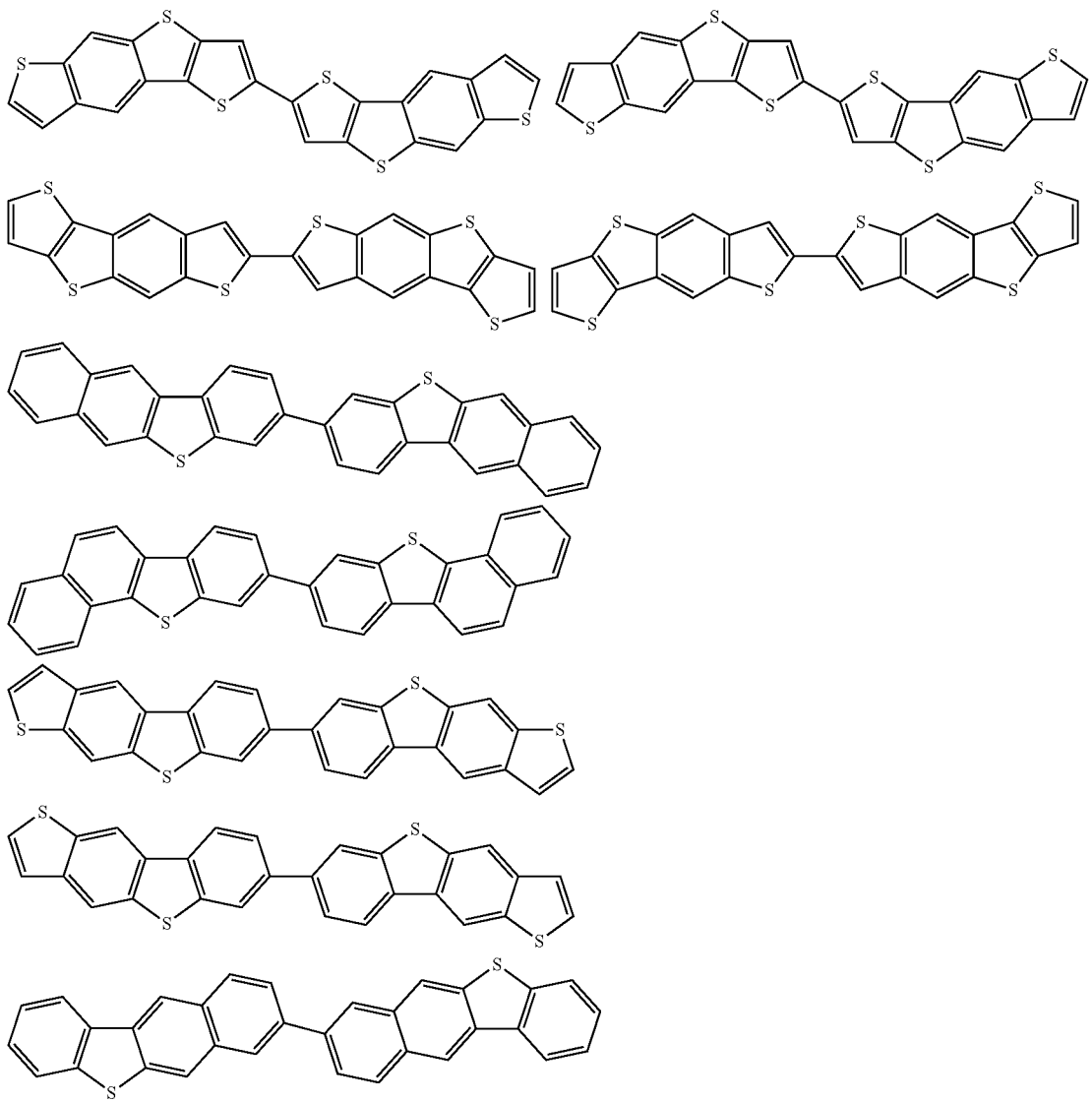

-continued
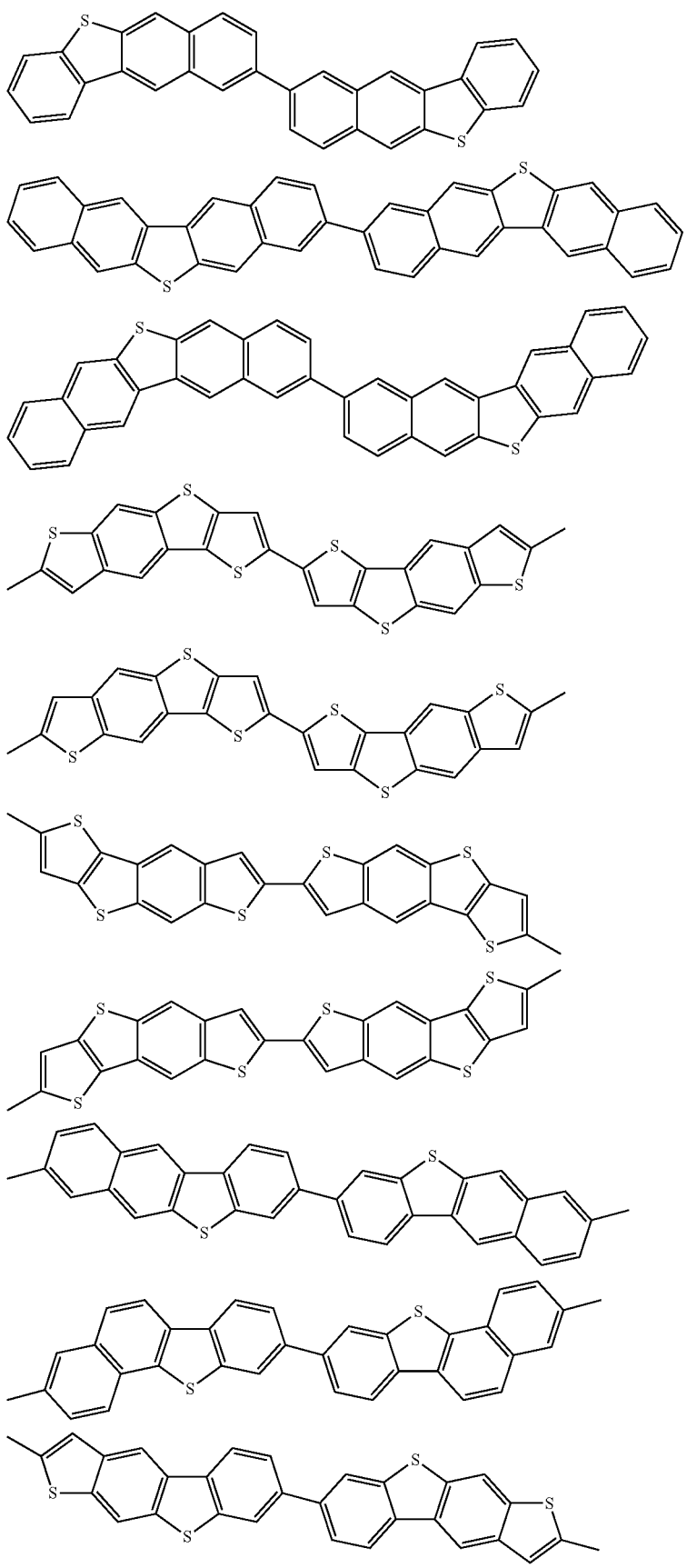

-continued
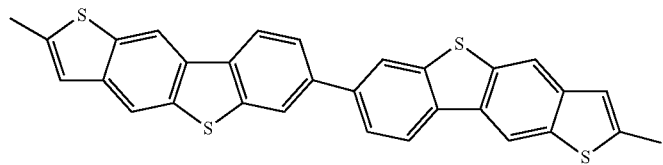
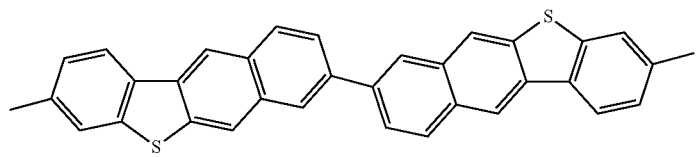
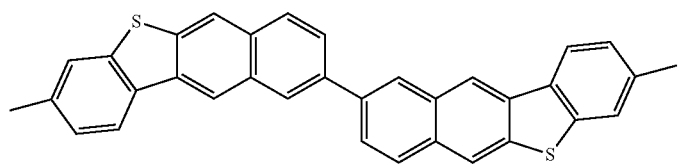
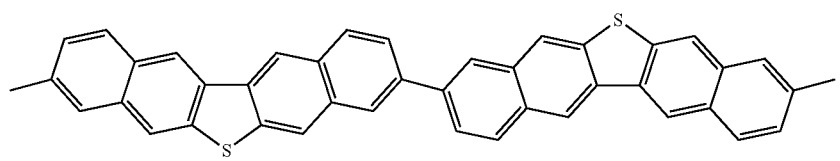
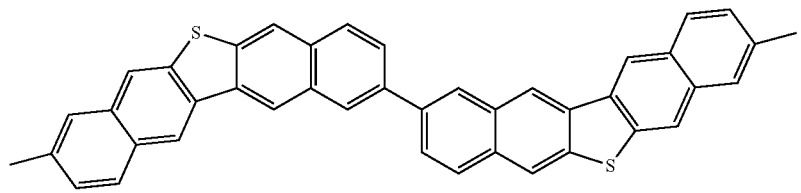
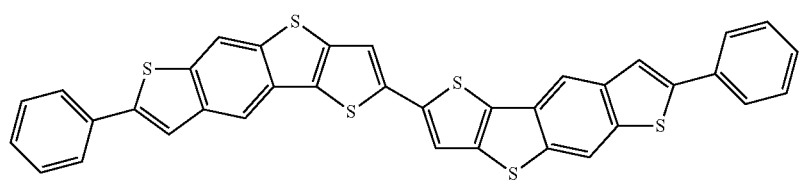
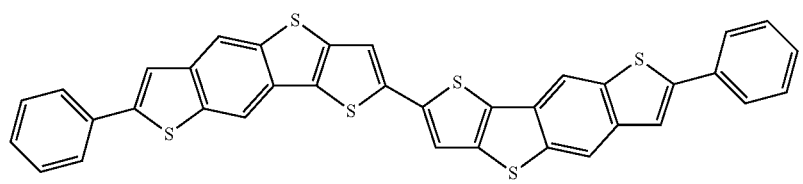
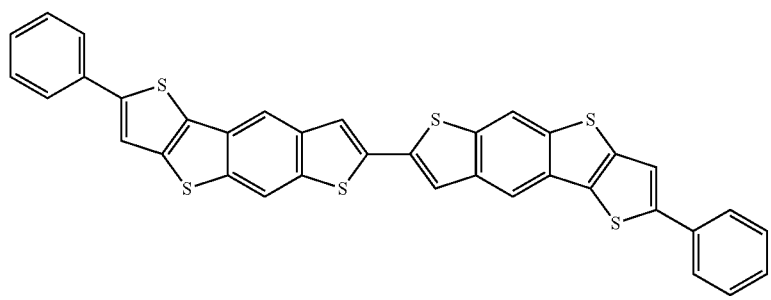

-continued
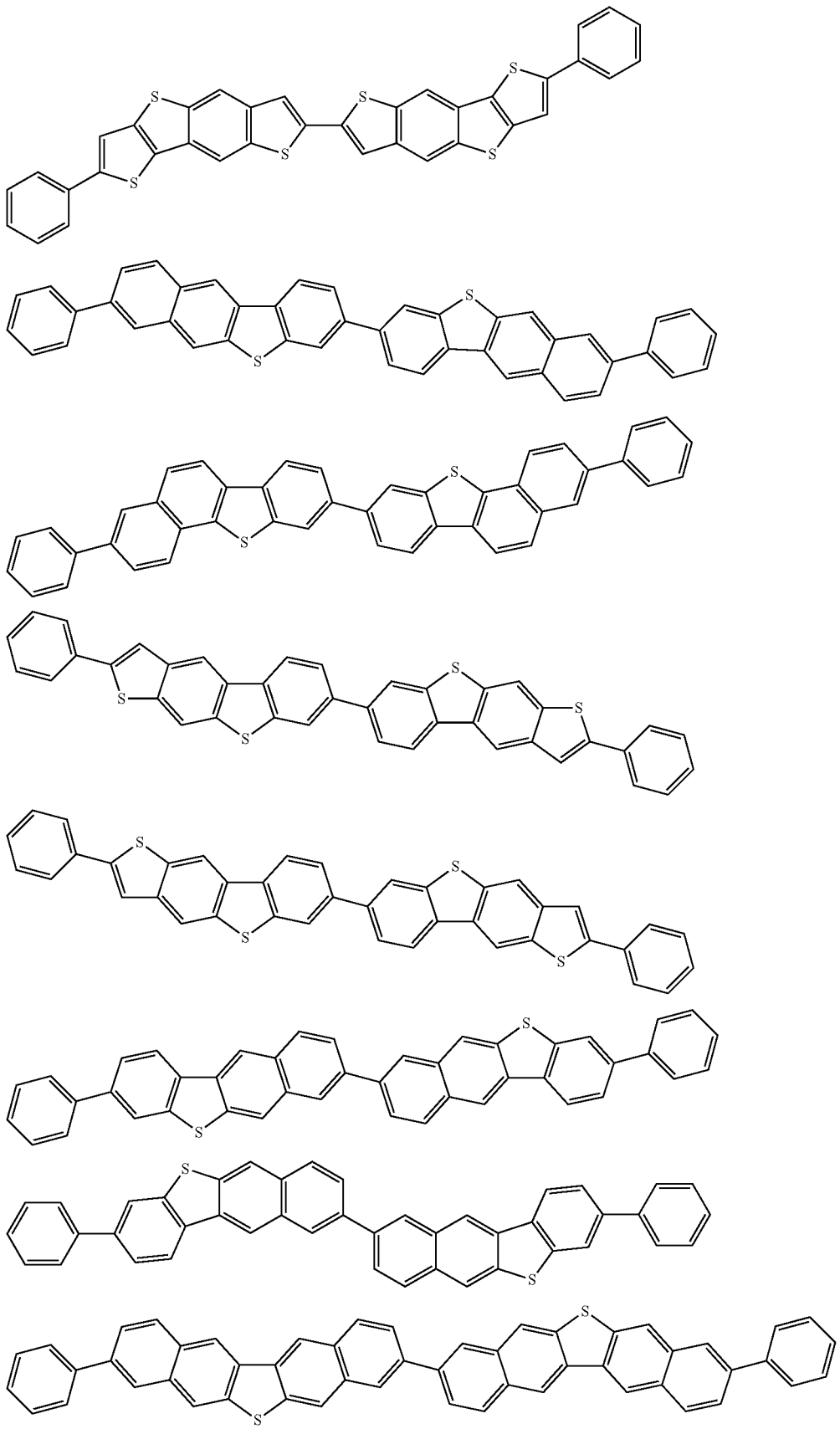

-continued

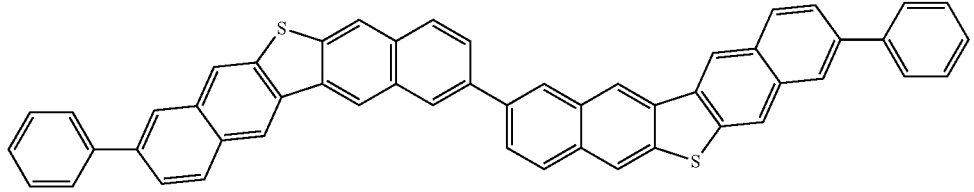

The gate electrode may include one of gold (Au), copper (Cu), nickel (Ni), aluminum (Al), molybdenum (Mo), chromium (Cr), tantalum (Ta), titanium (Ti), an alloy thereof, and a combination thereof.

The source electrode and the drain electrode may include at least one of gold (Au), copper (Cu), nickel (Ni), aluminum (Al), molybdenum (Mo), chromium (Cr), tantalum (Ta), titanium (Ti), an alloy thereof, and a combination thereof.

The organic thin film transistor may further include a gate insulating layer on the gate electrode.

The gate insulating layer may include one of a polyvinyl alcohol-based compound, a polyimide-based compound, a polyacryl-based compound, a polystyrene-based compound, benzocyclobutane (BCB)), a silicon nitride ($SiN_x$) and a silicon oxide ($SiO_x$).

According to example embodiments, an electronic device includes the organic thin film transistor.

The electronic device may include a liquid crystal display (LCD), an organic light emitting diode (OLED) device, an electrophoretic device, an organic photoelectric device, and an organic sensor.

According to example embodiments, an electronic device includes the organic thin film.

BRIEF DESCRIPTION OF THE DRAWING

FIG. 1 is a cross-sectional view of an organic thin film transistor according to example embodiments.

DETAILED DESCRIPTION

Example embodiments will hereinafter be described in detail, and may be easily performed by those who have common knowledge in the related art. However, this disclosure may be embodied in many different forms and is not construed as limited to the example embodiments set forth herein.

In the drawing, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawing, parts having no relationship with the description are omitted for clarity of the embodiments, and the same or similar constituent elements are indicated by the same reference numerals throughout the specification.

It will be understood that when an element or layer is referred to as being "on," "connected to," "coupled to," or "covering" another element or layer, it may be directly on, connected to, coupled to, or covering the other element or layer, or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It will be understood that, although the terms first, second, third, etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the example embodiments.

Spatially relative terms, e.g., "beneath," "below," "lower," "above," "upper," and the like, may be used herein for ease of description to describe one element or feature's relationship to another element(s) or feature(s) as illustrated in the FIGURES. It will be understood that the spatially relative terms are intended to encompass different orientations of the device in use or operation in addition to the orientation depicted in the FIGURES. For example, if the device in the FIGURES is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of the example embodiments. As used herein, the singular forms "a," "an," and "the" are intended to include the plural forms as well, unless the context clearly indicates otherwise. It will be further understood that the terms "comprises," "comprising," "includes," and/or "including," if used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As used herein, when a definition is not otherwise provided, the term "substituted" refers to one substituted with a substituent selected from a halogen atom (F, Br, Cl, or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, phosphoric acid or a salt thereof, a $C_1$ to $C_{20}$ alkyl group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_{20}$ alkoxy group, a $C_1$ to $C_{20}$ heteroalkyl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, a $C_3$ to $C_{30}$ heterocycloalkyl group, and a combination thereof, instead of hydrogen of a compound.

As used herein, when a definition is not otherwise provided, the term "hetero" refers to one including 1 to 3 heteroatoms selected from N, O, S, Se, and P.

Hereinafter, an organic compound according to example embodiments is described.

An organic compound according to example embodiments is represented by the Chemical Formula 1.

A-B            [Chemical Formula 1]

In Chemical Formula 1, each of an A moiety and a B moiety are independently a condensed polycyclic group having four or more fused rings, and are represented by one of the Chemical Formulae 2 to 4,

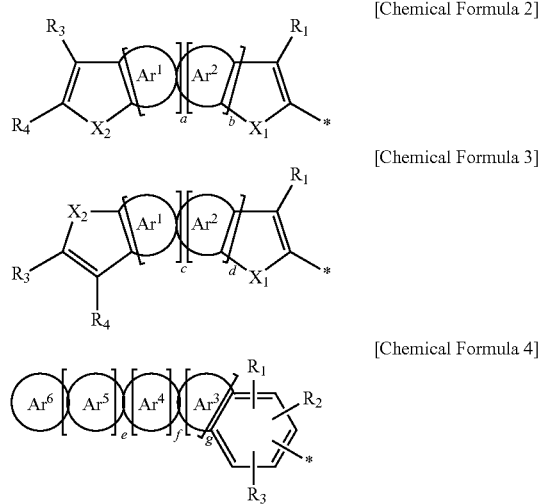

[Chemical Formula 2]

[Chemical Formula 3]

[Chemical Formula 4]

wherein, in Chemical Formulae 2 to 4, each of $Ar^1$ to $Ar^6$ are independently one of a substituted or unsubstituted 5-membered ring and a substituted or unsubstituted 6-membered ring, at least one of $Ar^3$ to $Ar^6$ is a substituted or unsubstituted 5-membered ring having a heteroatom, each of $Ar^1$ and $Ar^2$ forms a fused ring with an adjacent ring, each of $Ar^3$ to $Ar^6$ forms a fused ring with an adjacent ring, each of $X^1$ and $X^2$ are independently one of O, S, Se, Te, and $NR^a$, each of $R^1$ to $R^4$ and $R^a$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heteroaryl group, a substituted or unsubstituted $C_2$ to $C_{30}$ alkenyl group, a substituted or unsubstituted $C_2$ to $C_{30}$ alkynyl group, a hydroxy group, a halogen atom, and a combination thereof, each of a to g are independently integers ranging from 0 to 3, provided that a+b≥2, c+d≥2, and e+f+g≥2, and

* indicates a linking point.

The organic compound is a low molecular compound where the A moiety of a condensed polycyclic group having four or more fused rings and the B moiety of a condensed polycyclic group having four or more fused rings are linked to each other through a single bond. The organic compounds may increase charge mobility by appropriately adjusting the number of rings in the polycyclic groups and thereby increasing planarization properties of the organic compound and packing and stacking properties among the compounds. The organic compound may increase charge mobility by linking the two condensed polycyclic groups through a single bond and thereby increasing an orbital overlap among compounds. Herein, the A moiety and the B moiety may not be positioned on the same plane but may be twisted with a predetermined or given angle.

An organic compound having a structure in which the A moiety and the B moiety are linked by a single bond may be easily synthesized and highly dissolved as well as maintain an overlap among compounds, compared with a compound having a structure in which the A moiety and the B moiety are fused to each other. Accordingly, a yield of the organic compound may be increased and may be more easily applied to a solution process during formation of an organic thin film.

Each of the A moiety and the B moiety is a fused ring of a substituted or unsubstituted benzene ring and a substituted or unsubstituted heterocyclic group.

At least one of the $Ar^1$ and $Ar^2$ may be a heterocyclic group including one of O, S, Se, Te, and $NR^a$, and at least one of the $Ar^3$ to $Ar^6$ may be a heterocyclic group including one of O, S, Se, Te, and $NR^a$. Herein, $R^a$ is one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heteroaryl group, a substituted or unsubstituted $C_2$ to $C_{30}$ alkenyl group, a substituted or unsubstituted $C_2$ to $C_{30}$ alkynyl group, a hydroxy group, a halogen atom, and a combination thereof.

For example, the $Ar^1$ and $Ar^2$ of Chemical Formula 2 or 3 may be different, and for example one of $Ar^1$ and $Ar^2$ may be a substituted or unsubstituted benzene ring, and the other one may be a substituted or unsubstituted heterocyclic group.

For example, one of $Ar^3$ to $Ar^6$ of Chemical Formula 4 may be different from the others. For example, $Ar^3$ and $Ar^4$ may be the same and may be different from $Ar^5$, wherein $Ar^3$ and $Ar^4$ may be a substituted or unsubstituted heterocyclic group, and $Ar^5$ may be a substituted or unsubstituted benzene ring. For example, $Ar^4$ and $Ar^5$ may be the same and may be different from AP, wherein $Ar^4$ and $Ar^5$ may be a substituted or unsubstituted benzene ring, and $A^3$ may be a substituted or unsubstituted heterocyclic group. For example, $Ar^3$ and $Ar^5$ may be the same or may be different from $Ar^4$, wherein $Ar^3$ and $Ar^5$ may be a substituted or unsubstituted benzene ring and $Ar^4$ may be a substituted or unsubstituted heterocyclic group, or $Ar^3$ and $Ar^5$ may be a substituted or unsubstituted heterocyclic group and Ar₄ may be a substituted or unsubstituted benzene ring.

The A moiety and the B moiety may be the same or different.

Each of the A moiety and the B moiety may independently be, for example, one of the compounds listed in the Group 1, but are not limited thereto.

[Group 1]

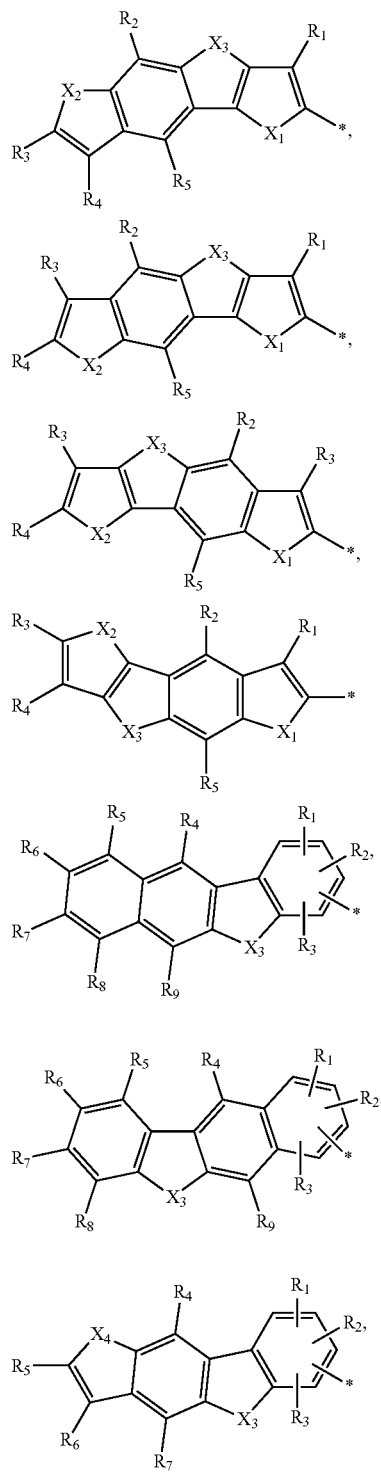

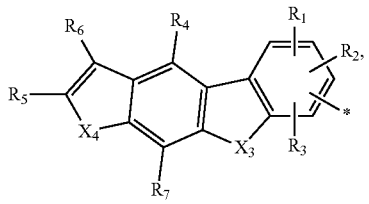

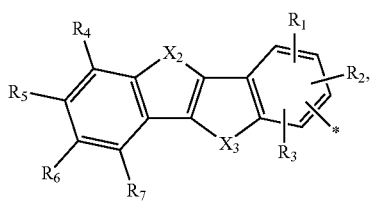

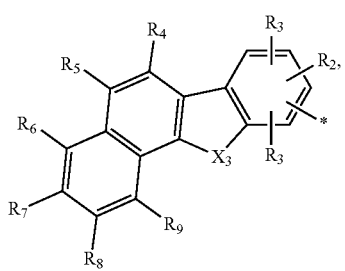

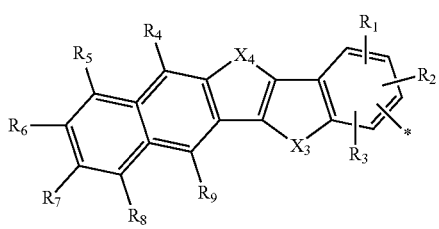

In Group 1, each of $X^1$ to $X^4$ are independently one of O, S, Se, Te, and $NR^a$, each of $R^1$ to $R^9$ and $R^a$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heteroaryl group, a substituted or unsubstituted $C_2$ to $C_{30}$ alkenyl group, a substituted or unsubstituted $C_2$ to $C_{30}$ alkynyl group, a hydroxy group, a halogen atom, and a combination thereof, each of $R^1$ to $R^9$ are independently present or two adjacent groups are fused to each other to provide a fused ring, and

* indicates a linking point.

The organic compound may be, for example, one of compounds listed in the Group 2, but is not limited thereto.

[Group 2]
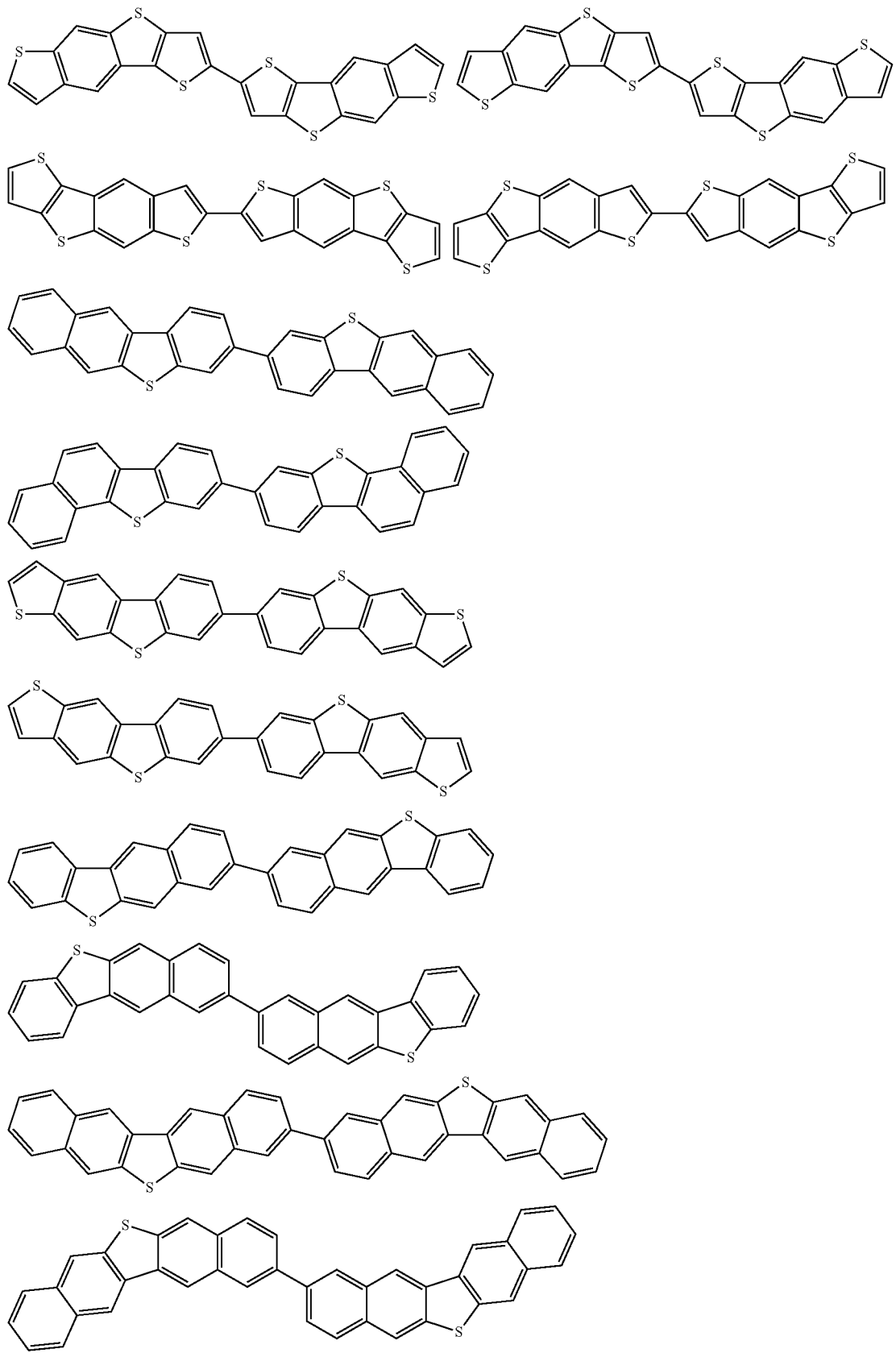

-continued
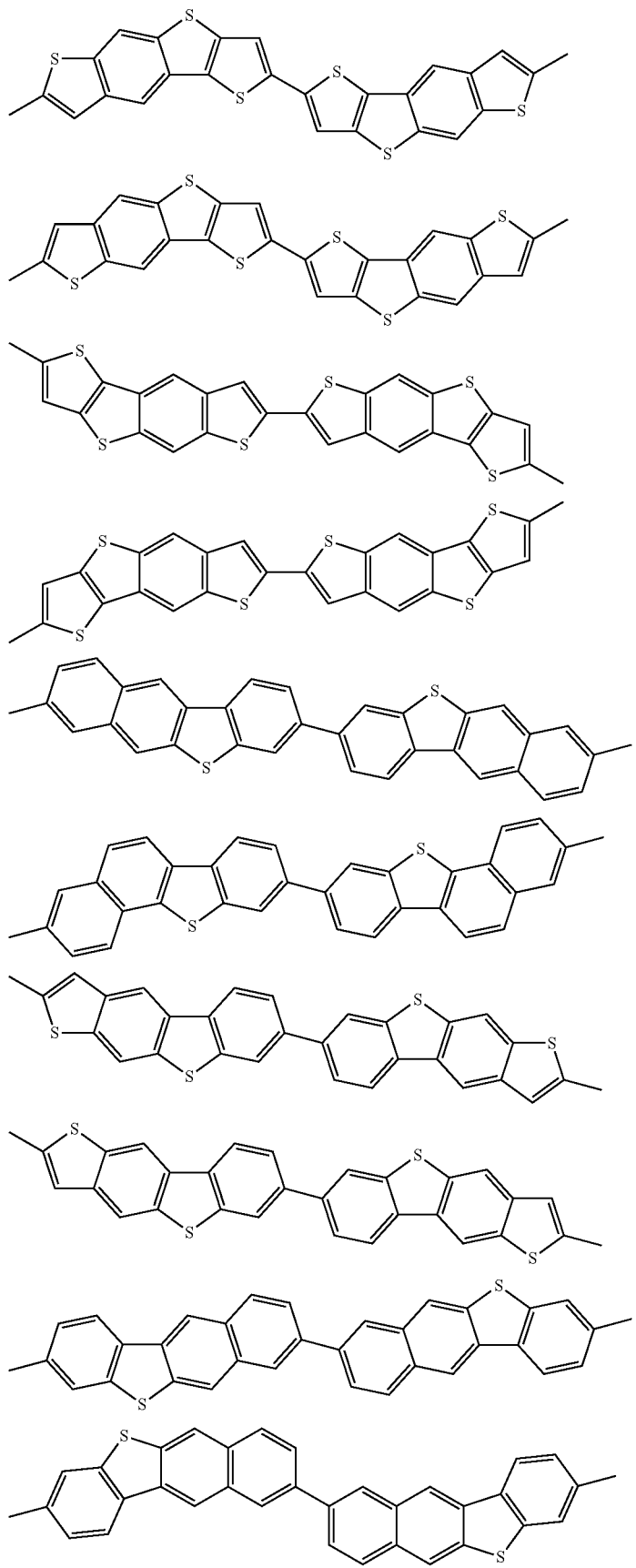

-continued
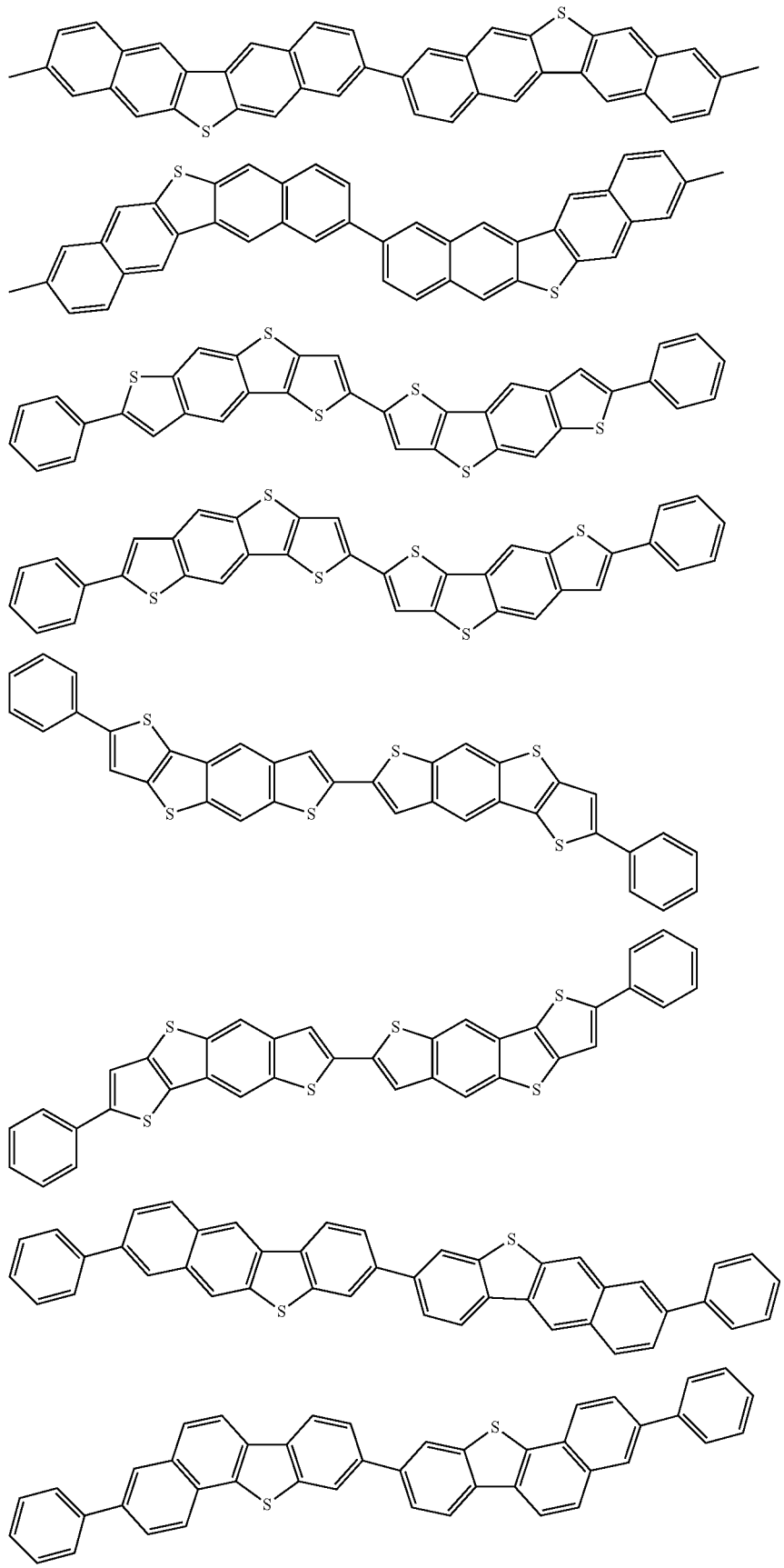

-continued

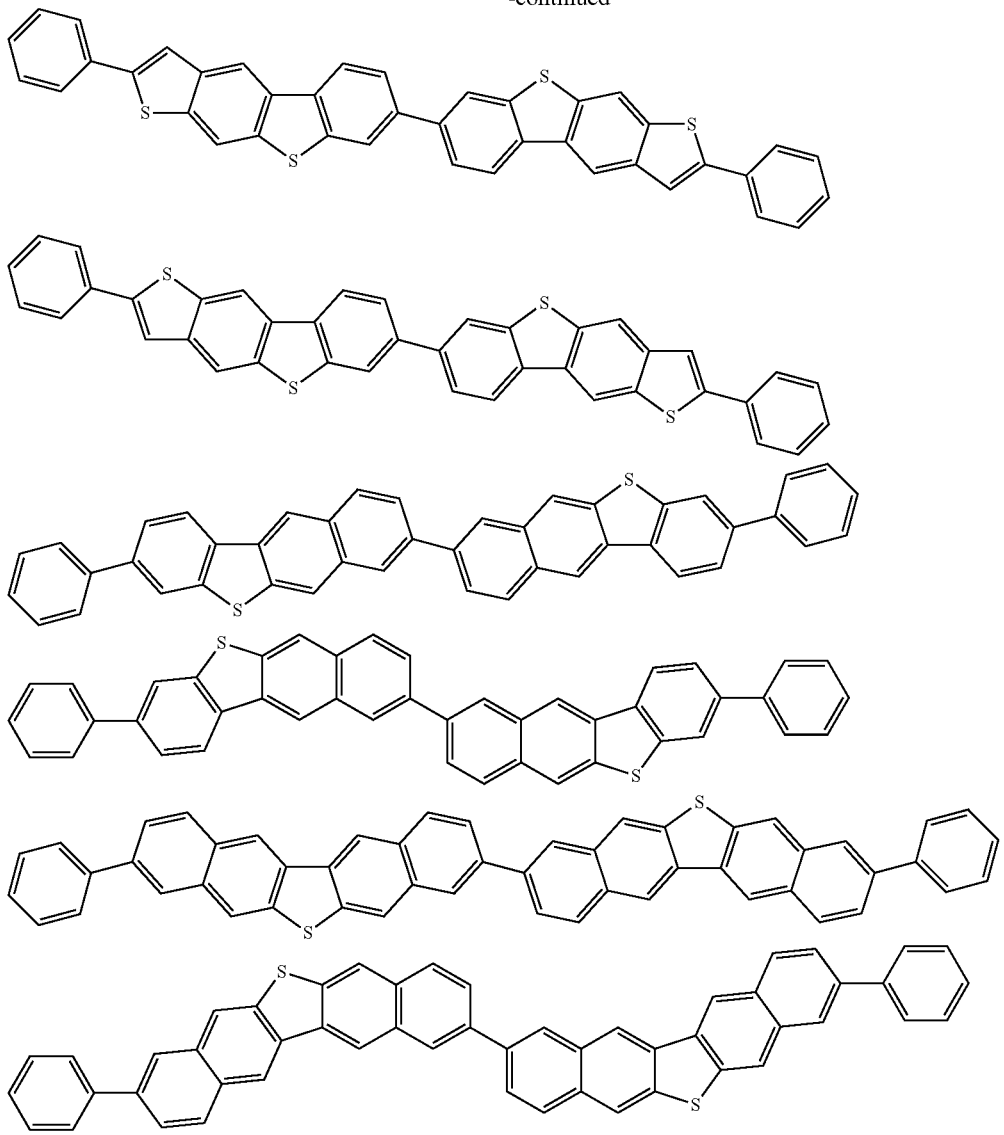

The organic compound may be formed into an organic thin film by a deposition or solution process. The organic thin film may be applied to various devices including an organic semiconductor. For example, the organic compound may be applied to an organic thin film transistor, and may be applied to a charge transport layer and/or an active layer of an electronic device (e.g., a solar cell, an organic light emitting diode (OLED) display, and an organic sensor).

Hereinafter, one example of an organic thin film transistor including the organic compound is described referring to the drawing.

In the drawing, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

FIG. 1 is a cross-sectional view of an organic thin film transistor according to example embodiments.

A gate electrode 124 is formed on a substrate 110 made of transparent glass, silicon, or plastic. The gate electrode 124 is connected to a gate line (not shown) transferring a gate signal. The gate electrode 124 may be made of gold (Au), copper (Cu), nickel (Ni), aluminum (Al), molybdenum (Mo), chromium (Cr), tantalum (Ta), titanium (Ti), an alloy thereof, or a combination thereof.

A gate insulating layer 140 is formed on the gate electrode 124. The gate insulating layer 140 may be made of an organic material or an inorganic material. Examples of the organic material may include a soluble polymer compound (e.g., a polyvinyl alcohol-based compound, a polyimide-based compound, a polyacryl-based compound, a polystyrene-based compound, and benzocyclobutane (BCB)), and examples of the inorganic material may include a silicon nitride ($SiN_x$) and a silicon oxide ($SiO_x$).

A source electrode 173 and a drain electrode 175 are formed on the gate insulating layer 140. The source electrode 173 and the drain electrode 175 face each other with the gate electrode 124 therebetween. The source electrode 173 is electrically connected to the data line (not shown)

transferring the data signal. The source electrode 173 and the drain electrode 175 may include at least one metal selected from gold (Au), copper (Cu), nickel (Ni), aluminum (Al), molybdenum (Mo), chromium (Cr), tantalum (Ta), titanium (Ti), an alloy thereof, or a combination thereof.

An organic semiconductor 154 is formed on the source electrode 173 and the drain electrode 175. The organic semiconductor 154 may be made of the organic compound. The organic semiconductor 154 may be formed in a solution process (e.g., spin coating, slit coating, or inkjet printing) by preparing the above organic semiconductor as a solution. However, the organic compound may be formed using a dry process (e.g., deposition).

Although the bottom gate structured organic thin film transistor is exemplified as an organic thin film transistor, it is not limited thereto, and it may be applied to all organic thin film transistors, for example, a top gate structured organic thin film transistor.

The organic thin film transistor may be applied to a switch or driving device of various electronic devices, and the electronic device may be, for example, a liquid crystal display (LCD), an organic light emitting diode (OLED) display, an electrophoretic display device, or an organic sensor.

Hereinafter, the present disclosure is illustrated in more detail with reference to examples. However, these are examples, and the present disclosure is not limited thereto.

Synthesis of Organic Compound

Synthesis Example 1

[Reaction Scheme 1]

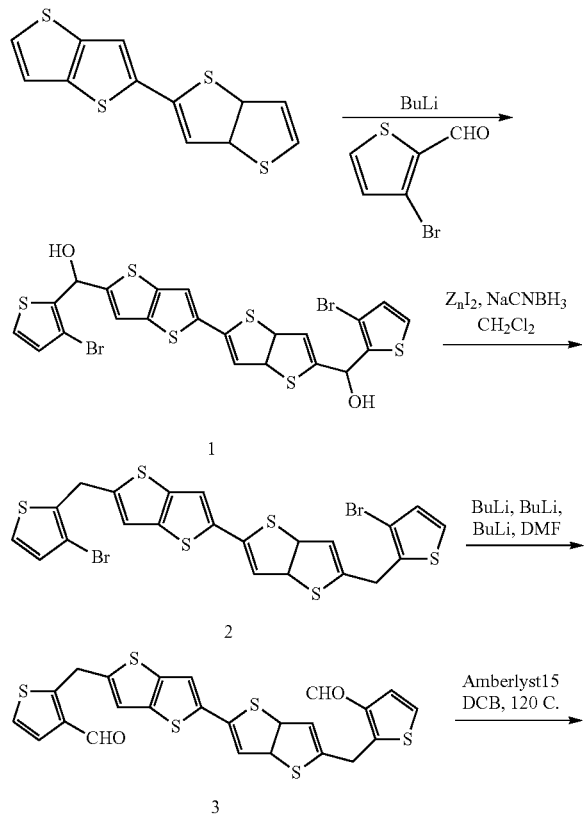

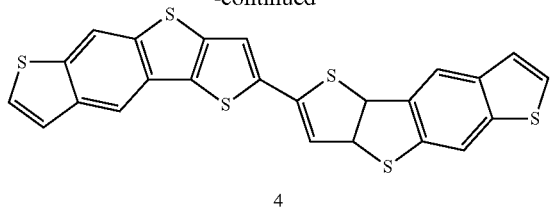

(1) Synthesis of 2,2'-bis[[1-hydroxy-(3-bromo-2-thienyl)methyl]-5,5'-bibenzothiophene] (Intermediate 1)

5.8 g (21 mmol) of bis-thieno[3,2:b]thiophene is dissolved in 500 ml of dry ether, the solution is added to 100 ml of a dry ether solution including butyl lithium cooled down to 0° C. (13 ml of a 2.5 M in hexane) in a dropwise fashion, and the mixture is slowly heated up and agitated at room temperature for 2 hours. Then, 5.2 g (27 mmol) of 3-bromothiophene-2-aldehyde is slowly added in a dropwise fashion to the cloudy solution, and the mixture is agitated overnight. Subsequently, 100 mL of an ammonium chloride-saturated solution is added thereto, and a precipitate therein is filtered and washed with water and ether, obtaining an intermediate 1. The yield is 60%.

$^1$H-NMR (500 MHz, CDCl$_3$): δ ppm 7.33 (d, 2H), 7.29 (s, 2H), 7.28 (s, 2H), 6.98 (d, 2H), 6.40 (d, 2H), 2.80 (s, 2H).

(2) Synthesis of 2,2'-bis[[(3-bromo-2-thienyl)methyl]-5,5'-bibenzothiophene] (intermediate 2)

2.9 g (4.5 mmol) of the intermediate 1 is dissolved in 200 mL of dichloromethane (CH$_2$Cl$_2$), and 2.3 g (7.3 mmol) of ZnI$_2$ and 2.0 g (32 mmol) of NaCNBH$_3$ are slowly added thereto. The mixture is agitated at room temperature for 24 hours, and then passed through a Celite pad. The filtered solution is respectively washed with an ammonium chloride-saturated solution and water, dried with MgSO$_4$, and concentrated under a reduced pressure, obtaining a yellow oil. The yellow oil is purified through silica chromatography, obtaining an intermediate 2. The yield is 70%.

$^1$H-NMR (500 MHz, CDCl$_3$): δ ppm 7.32 (d, 2H), 7.25 (s, 2H), 7.21 (s, 2H), 6.97 (d, 2H), 4.40 (s, 4H).

(3) Synthesis of 2,2'-bis[[(3-formyl-2-thienyl)methyl]-5,5'-bibenzothiophene] (intermediate 3)

A THF solution (100 mL) in which 3.2 g (10.5 mmol) of the intermediate 2 is dissolved is slowly added to an ether solution (200 mL) obtained by dissolving t-butyl lithium (15 mmol) therein and cooled down to −78° C. in a dropwise fashion. Subsequently, the mixture is agitated at −78° C. for about 30 minutes, 1.2 g of DMF is added thereto, and the obtained mixture is agitated for about 2 hours. Subsequently, after completing the reaction by pouring water therein, 200 mL of ethyl acetate is added thereto, and the obtained organic layer is washed with water and brine and then dried with MgSO$_4$ and concentrated under a reduced pressure, obtaining a colorless oil. The colorless oil is purified through silica chromatography, obtaining an intermediate 3. The yield is 60%.

$^1$H-NMR (500 MHz, CDCl$_3$): δ ppm 10.1 (s, 2H), 7.39 (s, 2H), 7.29 (d, 2H), 7.17 (s, 2H), 7.14 (s, 2H), 7.06 (d, 2H), 4.74 (s, 4H).

(4) Synthesis of 2,2'-bis[benzothieno[6,5-f]thieno[3,2-b]thiophene]] (compound 4)

0.9 g of the intermediate 3 is dissolved in 50 mL of 1,2-dichlorobenzene, and 0.9 g of Amberlyst 15 is added thereto. The mixture is heated up to 130° C. for 12 hours through a microwave reactor. Subsequently, an ivory solid compound 4 is obtained by cooling the mixture down to precipitate the Amberlyst 15 and then filtering it after removing a floating matter therefrom. The yield is 50%.

1H NMR (300 MHz, CDCl3): δ ppm 8.32 (d, 2H), 7.50 (d, 2H), 7.47 (d, 2H), 7.43 (d, 2H), 7.32 (d, 2H).

Synthesis Example 2

[Reaction Scheme 2]

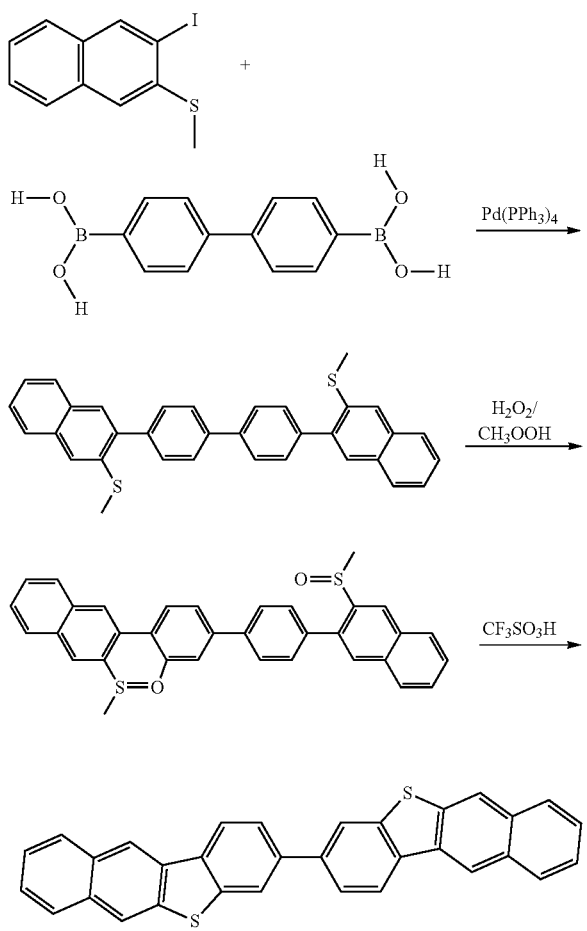

(1) Synthesis of 4,4'-bis(3-methylthio)naphthalene-2-yl)biphenyl 5.97 g (0.043 mol) of $K_2CO_3$ is put in a 3-necked flask under a nitrogen atmosphere, 60 ml of distilled water is added thereto, and then 100 ml of THF is added thereto. Then, 5 g (0.0148 mol) of 3-(methylthio)-2,3-dihydornaphthalene-2-yl trifluoromethane sulfonate and 0.0061 ml of biphenyl-4,4'-diboronic acid are added to the solution, 1.07 g (0.00093 mol) of tetrakis(triphenylphosphine)palladium (0) is added thereto, and the mixture is refluxed. After 5 hours, a 1N HCl solution is added thereto to complete the reaction, and the mixture is extracted with ethyl acetate. Subsequently, a solid obtained by drying the extract with MgSO4 to remove a solvent therefrom is washed several times, obtaining 2 g of a yellow solid 4,4'-(bis(3-methylthio)naphthalene-2-yl)biphenyl. The yield is 65%.

$^1$H-NMR (500 MHz, CDCl$_3$): δ ppm 7.89 (s, 1H), 7.79 (m, 2H), 7.62 (s, 1H), 7.49 (m, 1H), 7.44 (m, 1H), 7.29 (d, 1H), 7.26 (d, 1H), 2.55 (s, 3H).

(2) Synthesis of 4,4'-bis(3-methylsulfinyl)naphthalene-2-yl)biphenyl 1 g (0.00197 mol) of 4,4'-(bis(3-methylthio)naphthalene-2-yl)biphenyl obtained from the (1) is suspended in 100 ml of acetic acid, and then 0.46 g (0.0041 mol) of a 30% $H_2O_2$ solution is slowly added thereto. Subsequently, the mixture is agitated for 24 hours while heated at 40° C., and acetic acid is removed therefrom, obtaining 0.5 g of a yellow solid 4,4'-(bis(3-methylsulfinyl)naphthalene-2-yl)biphenyl.

$^1$H-NMR (500 MHz, CDCl$_3$): δ ppm 8.62 (s, 1H), 8.03 (m, 1H), 7.97 (s, 1H), 7.93 (m, 1H), 7.63 (m, 2H), 7.27 (d, 1H), 7.24 (m, 1H), 2.60 (s, 3H).

(3) Synthesis of 6,6'-binaphtho[2,3-b]benzo[2',3-d]thiophene 4,4'-(bis(3-methylsulfinyl)naphthalene-2-yl)biphenyl obtained from the (2) is added to 8 ml of trifluoromethane sulfonic acid, and the mixture is agitated for 24 hours. Subsequently, 80 ml of an $H_2O$/pyridine (8:1 v/v) solution is added to the solution, and the mixture is refluxed for 30 minutes. The obtained solid is filtered, obtaining an orange solid 4,4'-(bis(3-methylsulfinyl)naphthalene-2-yl)biphenyl.

Maldi-Mass (m/z): [M]+ calcd for $C_{32}H_{18}S_2$ 466.08; found 465.91.

Synthesis Example 3

[Reaction Scheme 3]

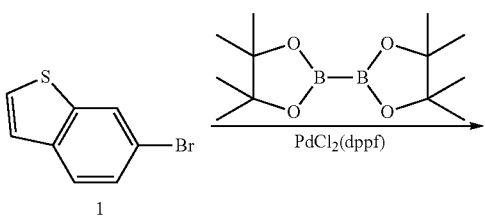

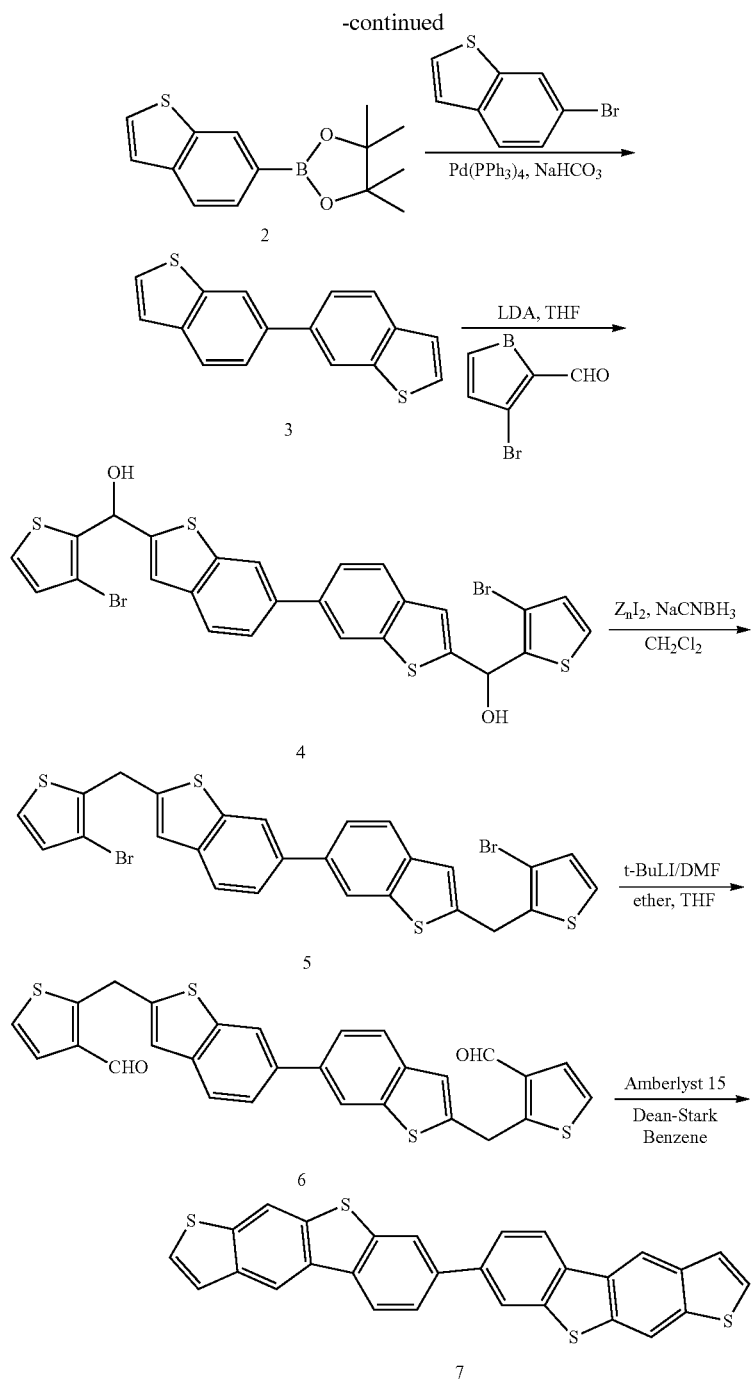

(1) Synthesis of 6-(4,4,5,5-tetramethyl-1,3,2-dioxaborolane-2-yl)benzothiophene 70 g (0.33 mol) of 6-bromo-benzo[b]thiophene (a compound 1), 92.2 g (1.1 eq) of bis(pinacolato)diboron, 14.5 g (6 mol %) of $PdCl_2(dppf)$, and 97 g (3 eq) of potassium acetate are refluxed and agitated with 1,4-dioxane under a nitrogen atmosphere. After being left overnight, the mixture is cooled down to room temperature and then concentrated. Then, the mixture is passed through a silica pad, obtaining a compound 2.

(2) Synthesis of 6,6'-bibenzothiophene 70 g (0.33 mol) of 6-bromo-benzo[b]thiophene, 0.33 mol (1 eq) of the compound 2, 19 g (5 mol %) of $Pd(PPh_3)_4$, and 83 g (3 eq) of sodium bicarbonate are refluxed and agitated with a mixed solvent of $DME/H_2O$. After 22 hours, the mixture is cooled down to room temperature and extracted with ethyl acetate and water. The obtained organic layer is treated with $MgSO_4$, and then filtered and concentrated, obtaining a solid compound. The solid compound is recrystallized, obtaining 70 g of a compound 3.

$^1$H-NMR (300 MHz, CDCl$_3$): δ ppm 8.15 (s, 2H), 7.89 (d, 2H), 7.66 (d, 2H), 7.45 (d, 2H), 7.36 (d, 2H)

(3) Synthesis of 2,2'-bis[(3-bromo-2-thienyl)-hydroxymethyl]-6,6'-bibenzothiophene LDA (2.2 eq) is agitated in a THF solvent under a nitrogen atmosphere. A solution obtained by dissolving the compound 3 in THF at −10° C. is added thereto in a dropwise fashion. The mixture is agitated for one hour, while being maintained at −5° C. to 0° C., and then cooled down to −78° C. Then, 94 g (2.5 eq) of 3-bromothiophene-2-carbaldehyde dissolved in a small amount of THF is added thereto in a dropwise fashion, and the temperature of the obtained mixture is slowly increased up to room temperature. When the reaction is complete, the resultant is quenched with sat. NH$_4$Cl and then extracted with ethyl acetate and water. The obtained organic layer is treated with MgSO$_4$, and then filtered and concentrated. Subsequently, the concentrated product is column-purified, obtaining a compound 4.

$^1$H-NMR (300 MHz, CDCl$_3$): δ ppm 8.04 (s, 2H), 7.78 (d, 2H), 7.62 (d, 2H), 7.32 (d, 2H), 7.29 (s, 2H), 6.98 (d, 2H), 6.49 (d, 2H), 2.84 (d, 2H)

(4) Synthesis of 2,2'-bis[(3-bromo-2-thienyl)methyl]-6,6'-bibenzothiophene

The compound 4 is suspended in DCM, and 3.2 eq of ZnI$_2$ and 14 eq of NaBH$_3$CN are added thereto. The mixture is agitated overnight. When the reaction is complete, the reaction solution is filtered through a Celite pad. Then, a solid obtained after the concentration is recrystallized, obtaining 89 g of a compound 5.

$^1$H-NMR (300 MHz, CDCl$_3$): δ ppm 8.01 (s, 2H), 7.77 (d, 2H), 7.61 (d, 2H), 7.24 (d, 2H), 7.14 (s, 2H), 6.99 (d, 2H), 4.42 (s, 4H)

(5) Synthesis of 2,2'-bis[(3-formyl-2-thienyl)methyl]-6,6'-bibenzothiophene 20 g (32.44 mmol) of the compound 5 and 14.4 mL (4 eq) of 1-formylpiperidine are dissolved in THF under an argon environment, and the solution is cooled down to −78° C. Then, 85.8 mL (4.5 eq) of 1.7 M t-BuLi is slowly added thereto in a dropwise fashion, the mixture is agitated for 10 minutes, and then heated up to −30° C.

The resultant is poured into a sat. NH$_4$Cl solution for quenching and then extracted with ethyl acetate. The obtained organic layer is dried with MgSO4 and concentrated under a reduced pressure and then treated through column/recrystallization, obtaining 6.76 g of a compound 6.

$^1$H-NMR (300 MHz, CDCl$_3$): δ ppm 10.1 (s, 2H), 8.14 (s, 2H), 7.84 (d, 2H), 7.66 (d, 2H), 7.38 (d, 2H), 7.16 (s, 2H), 7.01 (d, 2H), 4.44 (s, 4H)

(6) Synthesis of 6,6'-bithienobenzo[5,6-b]benzo[2,3-d]thiophene

Benzene is added to 19.5 g (37.89 mmol) of the compound 6 under a nitrogen atmosphere, 29.3 g of Amberlyst 15 is added thereto, and water is removed from the mixture by using a Dean-Stark trap. Then, a floating matter is carefully removed therefrom and then filtered, obtaining 11.4 g of a light gray compound 7.

Maldi-Mass (m/z): [M]+ calcd for C$_{28}$H$_{14}$S$_4$ 478.00; found 477.81.

Manufacture of Organic Thin Film Transistor

Example 1

First, a silicon wafer substrate coated with the SiO$_2$ to be 3000 Å thick is exposed to O$_2$ plasma, and then dipped in an octadecyl trichlorosilane solution diluted in hexane to a concentration of 10 mM to change the surface to be hydrophobic. Subsequently, the organic compound according to Synthesis Example 2 is vacuum-vapor deposited to be 700 Å thick by heating the substrate from room temperature to 200° C. Subsequently, source and drain electrodes are formed thereon by using a shadow mask and depositing Au to be 1000 Å thick, manufacturing an organic thin film transistor.

Example 2

An organic thin film transistor is manufactured according to the same method as Example 1, except for using the organic compound of Synthesis Example 3 instead of the organic compound of Synthesis Example 2.

Evaluation

Charge mobility and current on/off ratio (I$_{on}$/I$_{off}$) of the organic thin film transistors according to Example 1 and 2 are calculated.

The charge mobility of the organic thin film transistors is obtained by obtaining a graph having (I$_{SD}$)$^{1/2}$ and V$_G$ as variables from a saturation region current formula and a slope in the graph.

$$I_{SD} = \frac{WC_0}{2L}\mu(V_G - V_T)^2$$

$$\sqrt{I_{SD}} = \sqrt{\frac{\mu C_0 W}{2L}}(V_G - V_T)$$

$$\text{slope} = \sqrt{\frac{\mu C_0 W}{2L}}$$

$$\mu_{FET} = (\text{slope})^2 \frac{2L}{C_0 W}$$

In the equations, I$_{SD}$ is a source-drain current, μ or μ$_{FET}$ is charge mobility, C$_0$ is electrostatic capacity of a gate insulating layer, W is a channel width, L is a channel length, V$_G$ is a gate voltage, and V$_T$ is a threshold voltage.

A cut-off leakage current (I$_{off}$) is a current flowing in an off state, and obtained as a minimum current in an off state. A current on-off ratio (I$_{on}$/I$_{off}$) is obtained as a ratio of a maximum current in an on state relative to a minimum current in the off state.

The results are shown in Table 1.

TABLE 1

| | Charge mobility (cm$^2$/Vs) | Current on/off ratio (I$_{on}$/I$_{off}$) |
|---|---|---|
| Example 1 | 2.1 | 2.0 × 10$^7$ |
| Example 2 | 1.5 | 1.8 × 10$^7$ |

Referring to Table 1, the organic thin film transistors according to Example 1 and 2 show charge mobility of about 1 cm$^2$/Vs or greater and a current on/off ratio of about 1×10$^7$ or greater, which indicate improved characteristics when compared with a conventional thin film transistor.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. An organic compound represented by Chemical Formula 1:

A-B                        [Chemical Formula 1]

wherein, in Chemical Formula 1,
each of an A moiety and a B moiety are independently a condensed polycyclic heteroaromatic group having four or more fused rings, and are represented by Group I,

[Group I]

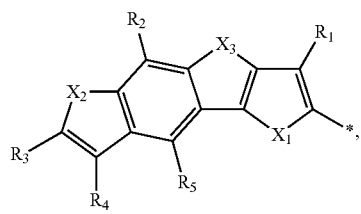

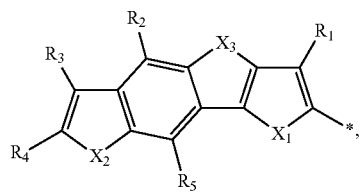

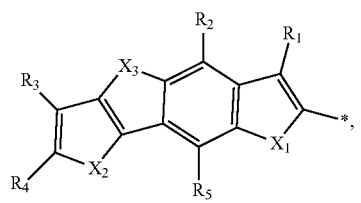

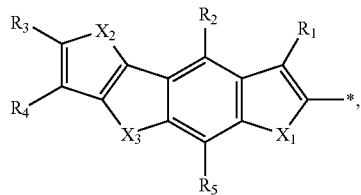

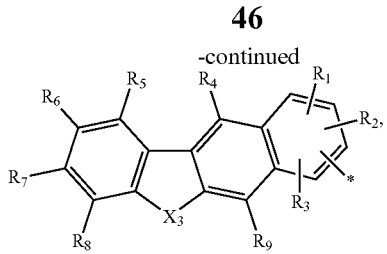

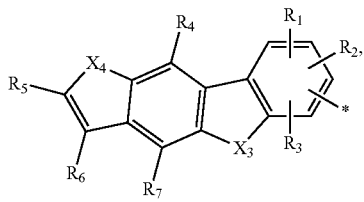

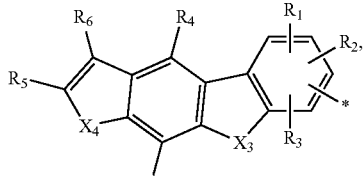

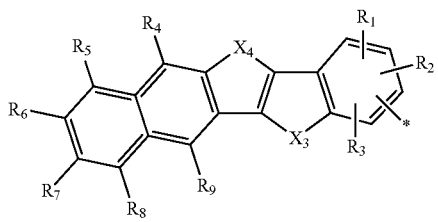

wherein,
each of $X^1$, $X^2$ $X^3$ to $X^4$ are independently one of O, S, Se, and Te, and
each of $R^1$ to $R^9$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heteroaryl group, a substituted or unsubstituted $C_2$ to $C_{30}$ alkenyl group, a substituted or unsubstituted $C_2$ to $C_{30}$ alkynyl group, a hydroxy group, a halogen atom, and a combination thereof.

2. The organic compound of claim 1, wherein the A moiety and the B moiety are not on the same plane in a molecule.

3. The organic compound of claim 1, wherein the organic compound is one of compounds listed in the Group 2:

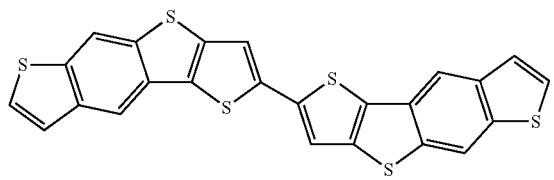

-continued
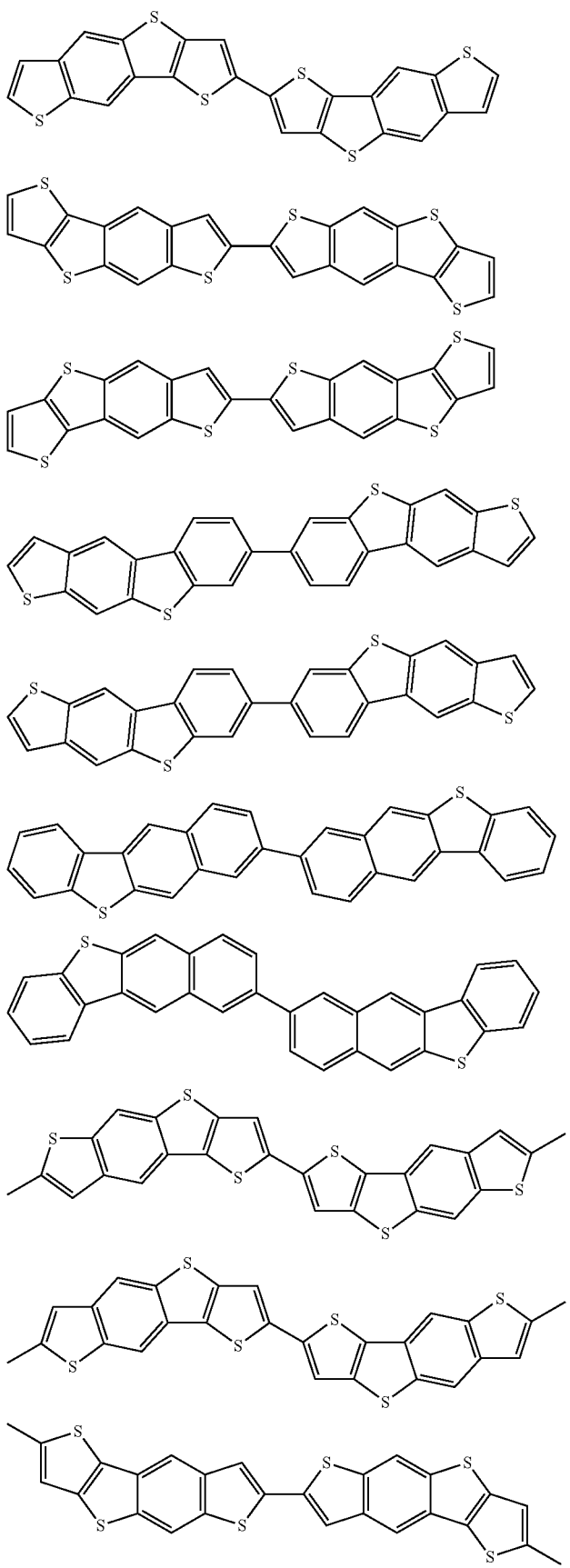

-continued
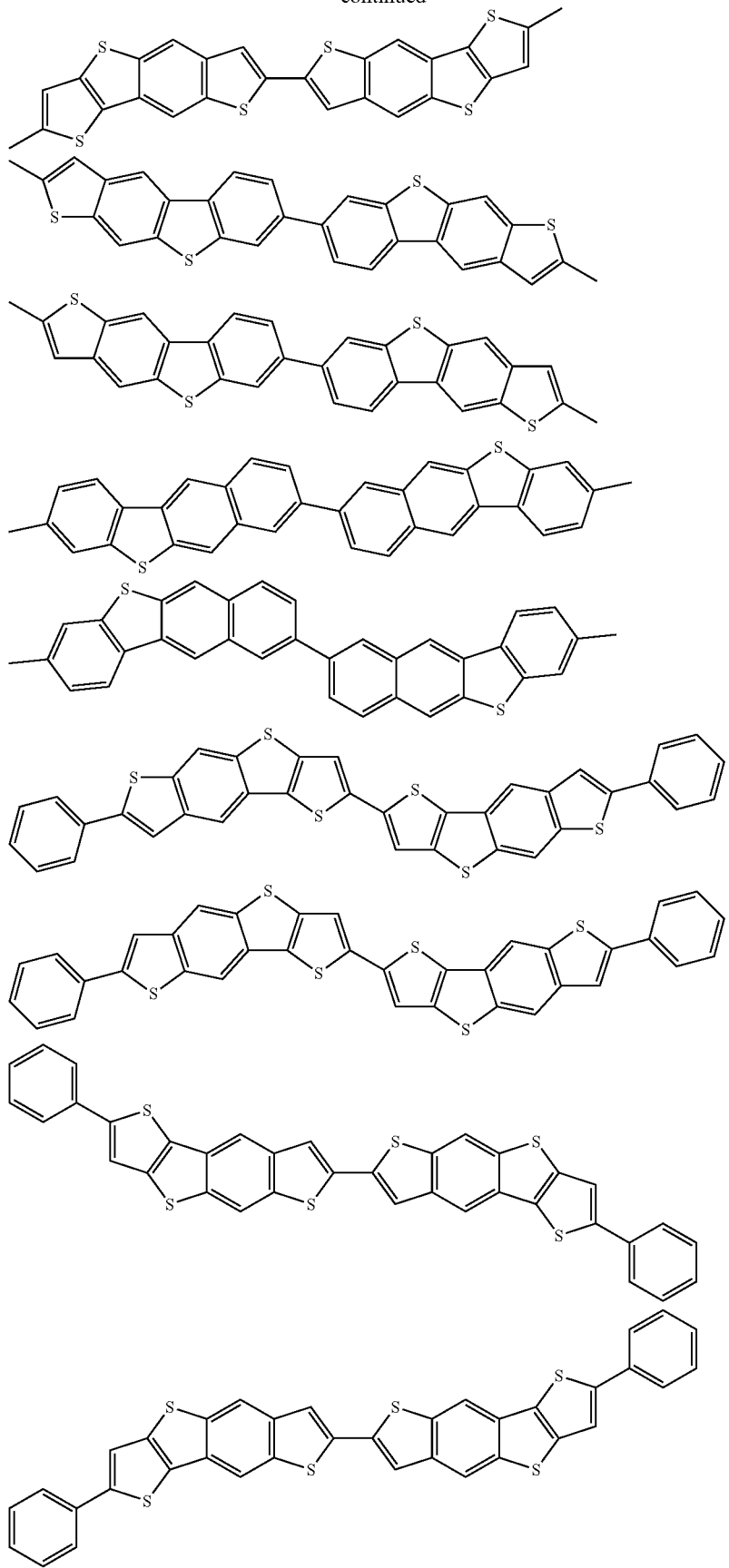

-continued
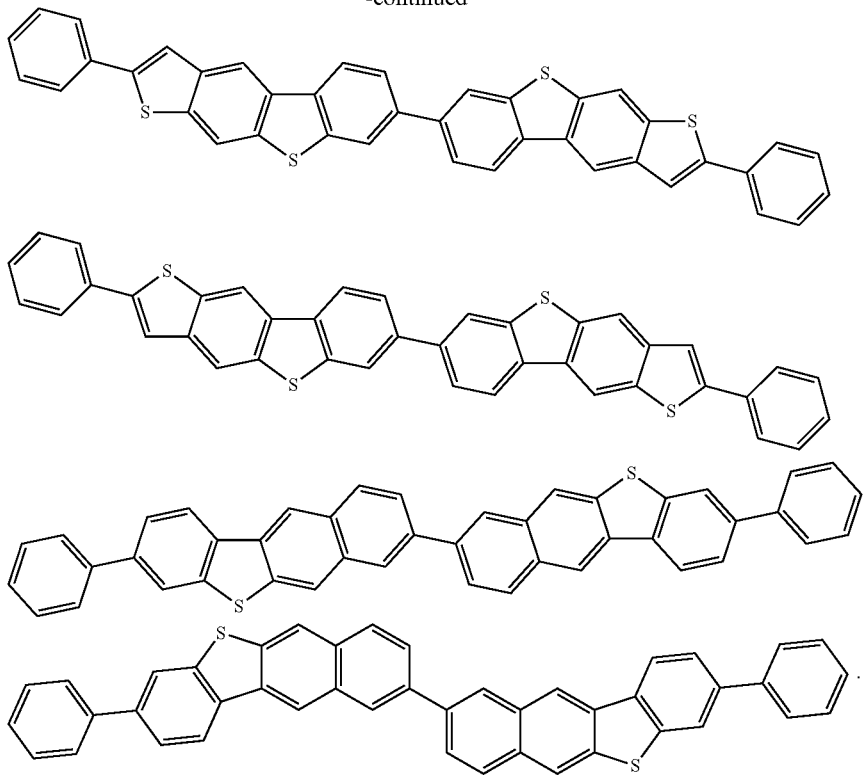
4. An organic film comprising the organic compound of claim 1.
5. An electronic device comprising the organic film of claim 4.
* * * * *